(12) United States Patent
Nakai et al.

(10) Patent No.: US 9,889,270 B2
(45) Date of Patent: Feb. 13, 2018

(54) METHOD OF CONTROLLING RELAXATION EQUIPMENT, CONTROL SYSTEM FOR RELAXATION EQUIPMENT, AND METHOD OF CREATING USER MODEL

(71) Applicant: Panasonic Corporation, Osaka (JP)

(72) Inventors: Kentaro Nakai, Hyogo (JP); Koichi Kusukame, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 720 days.

(21) Appl. No.: 14/358,071

(22) PCT Filed: Sep. 13, 2013

(86) PCT No.: PCT/JP2013/005440
§ 371 (c)(1),
(2) Date: May 14, 2014

(87) PCT Pub. No.: WO2014/050005
PCT Pub. Date: Apr. 3, 2014

(65) Prior Publication Data
US 2014/0303785 A1     Oct. 9, 2014

Related U.S. Application Data

(60) Provisional application No. 61/706,849, filed on Sep. 28, 2012.

(51) Int. Cl.
| | |
|---|---|
| *A61M 21/02* | (2006.01) |
| *G06F 19/12* | (2011.01) |
| *G06Q 50/22* | (2012.01) |
| *A61H 33/00* | (2006.01) |
| *G06F 19/00* | (2018.01) |
| *A61M 21/00* | (2006.01) |
| *A61M 16/16* | (2006.01) |

(Continued)

(52) U.S. Cl.
CPC ......... *A61M 21/02* (2013.01); *A61H 33/0095* (2013.01); *G06F 19/12* (2013.01);
(Continued)

(58) Field of Classification Search
CPC .. A61M 21/02; A61H 31/0095; G06F 189/12; G06F 19/3481; G06Q 50/22
See application file for complete search history.

(56) References Cited

U.S. PATENT DOCUMENTS

| | | |
|---|---|---|
| 7,955,259 B2 | 6/2011 | Lee et al. |
| 2005/0075532 A1 | 4/2005 | Lee et al. |

(Continued)

FOREIGN PATENT DOCUMENTS

| | | |
|---|---|---|
| JP | 2003-70772 | 3/2003 |
| JP | 2004-24879 | 1/2004 |

(Continued)

OTHER PUBLICATIONS

International Search Report dated Oct. 29, 2013 in International (PCT) Application No. PCT/JP2013/005440.

*Primary Examiner* — Charles E Anya
(74) *Attorney, Agent, or Firm* — Wenderoth, Lind & Ponack, L.L.P.

(57) ABSTRACT

A method of controlling relaxation equipment is a method of controlling relaxation equipment capable of changing a biological value of a user. The method includes: obtaining a user model including a transition in biological value within a period from a start time to an end time of a program being viewed by the user; obtaining a first biological value of the user viewing the program; and controlling the relaxation equipment such that the biological value of the user at the end time approximates a second biological value included in the user model, which is a value at the end time, based on the first biological value and the second biological value.

8 Claims, 17 Drawing Sheets

(51) Int. Cl.
*A61H 7/00* (2006.01)
*A61H 33/06* (2006.01)

(52) U.S. Cl.
CPC ......... *G06F 19/3481* (2013.01); *G06Q 50/22* (2013.01); *A61H 7/007* (2013.01); *A61H 2033/0079* (2013.01); *A61H 2033/068* (2013.01); *A61H 2201/0149* (2013.01); *A61H 2201/5007* (2013.01); *A61H 2201/5012* (2013.01); *A61H 2230/065* (2013.01); *A61H 2230/80* (2013.01); *A61M 16/161* (2014.02); *A61M 2021/0044* (2013.01); *A61M 2021/0066* (2013.01); *A61M 2205/3368* (2013.01); *A61M 2205/502* (2013.01); *A61M 2205/581* (2013.01); *A61M 2205/583* (2013.01); *A61M 2230/00* (2013.01); *A61M 2230/06* (2013.01)

(56) References Cited

U.S. PATENT DOCUMENTS

| | | | |
|---|---|---|---|
| 2006/0094934 A1 | 5/2006 | Shirai et al. | |
| 2006/0142968 A1* | 6/2006 | Han | A61B 5/0205 702/120 |
| 2006/0293838 A1 | 12/2006 | Yamamoto et al. | |
| 2008/0163416 A1* | 7/2008 | Go | E03C 1/055 4/559 |
| 2009/0235447 A1* | 9/2009 | Zack | A61H 33/06 4/524 |
| 2010/0249613 A1* | 9/2010 | Hashimoto | A61B 5/02405 600/485 |
| 2012/0131743 A1* | 5/2012 | Hayasi | A61H 33/06 4/524 |

FOREIGN PATENT DOCUMENTS

| | | | | |
|---|---|---|---|---|
| JP | 2005058299 A | * | 3/2005 | ............ A47K 3/00 |
| JP | 2005-128976 | | 5/2005 | |
| JP | 2006-115865 | | 5/2006 | |
| JP | 2006271602 A | * | 10/2006 | ............ A47K 4/00 |
| JP | 2007-26429 | | 2/2007 | |
| JP | 2007054501 A | * | 3/2007 | ............ A47K 4/00 |
| JP | 2007309476 A | * | 11/2007 | ............ F24H 1/00 |
| JP | 2010-104457 | | 5/2010 | |
| JP | 2010-253141 | | 11/2010 | |

* cited by examiner (a)

(b)

METHOD OF CONTROLLING RELAXATION EQUIPMENT, CONTROL SYSTEM FOR RELAXATION EQUIPMENT, AND METHOD OF CREATING USER MODEL

TECHNICAL FIELD

The present invention relates to a method of controlling relaxation equipment, a control system for the relaxation equipment, and a method of creating a user model.

BACKGROUND ART

Patent Literature 1 discloses a technique for adding information to a viewing program using user's biological information.

Moreover, Patent Literature 2 discloses a technique for collecting the biological information of a user without contact with the user, and changing the audio of content being played, according to the collected biological information.

CITATION LIST

Patent Literature

[PTL 1] Japanese Unexamined Patent Application Publication No. 2010-253141
[PTL 2] Japanese Unexamined Patent Application Publication No 2006-115865

SUMMARY OF INVENTION

Technical Problem

In some cases, a user who views a program while using relaxation equipment finishes viewing the program without being relaxed, depending on the program.

In view of the above problem, the present invention provides a method of controlling relaxation equipment for relaxing the user along with the progress of a program.

Solution to Problem

A method of controlling relaxation equipment according to one aspect of the present invention is a method of controlling relaxation equipment capable of changing a biological value of a user. The method includes: obtaining a user model including a transition in biological value within a period from a start time to an end time of a program; obtaining a first biological value of the user viewing the program; and controlling the relaxation equipment such that the biological value of the user at the end time approximates a second biological value included in the user model, which is a value at the end time, based on the first biological value and the second biological value.

It should be noted that general and specific aspect(s) disclosed above may be implemented using a system, a method, an integrated circuit, a computer program, or a computer-readable recording medium such as a CD-ROM, or any combination of systems, methods, integrated circuits, computer programs, or computer-readable recording media.

Advantageous Effects of Invention

The method of controlling relaxation equipment in the present invention enables a user to view a program in a relaxed state.

Figure 1:
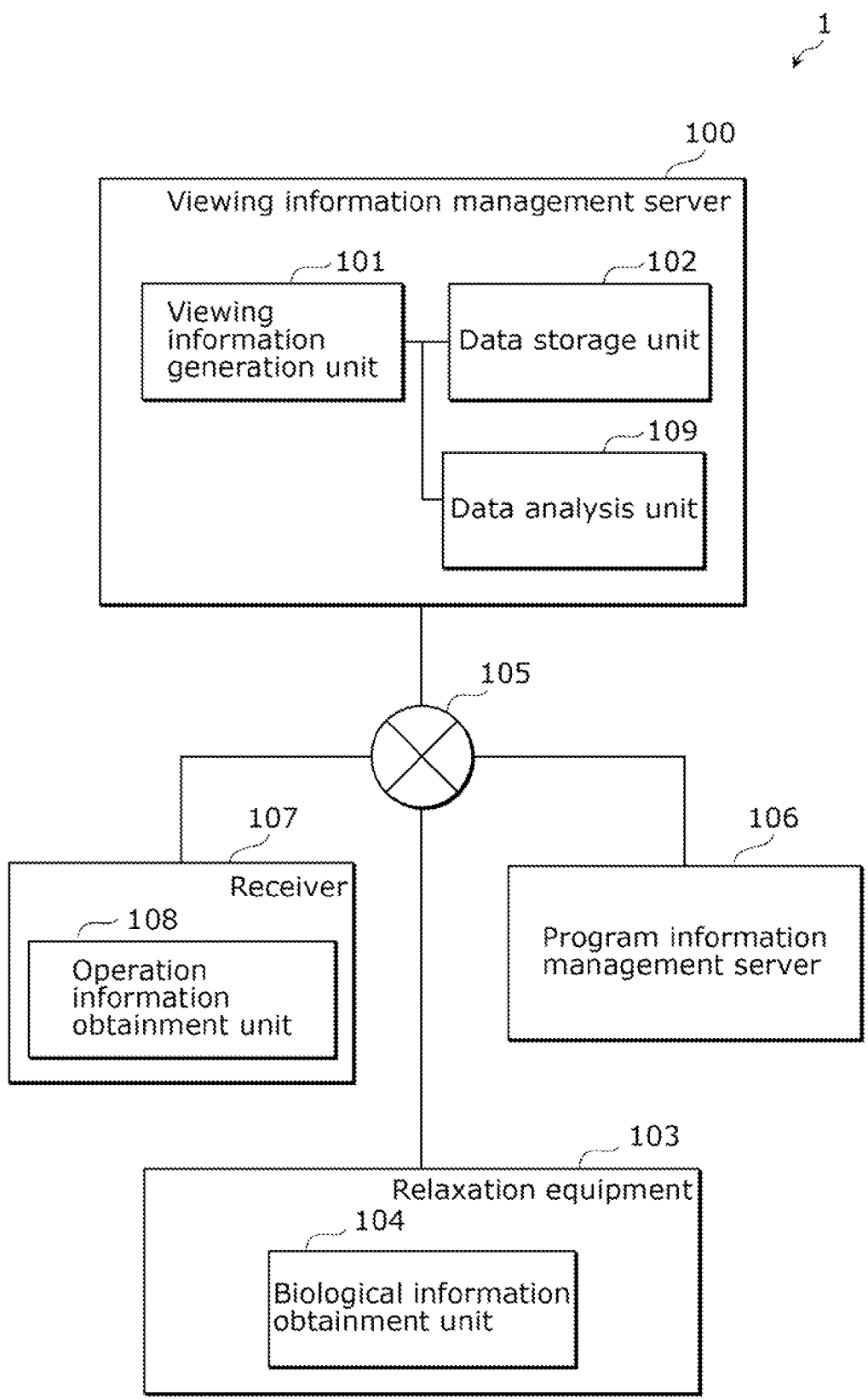
FIG. 1 is a network chart illustrating an example of a control system in Embodiment 1.

DESCRIPTION OF EMBODIMENTS (Underlying Knowledge Forming Basis of the Present Disclosure The inventors have found that the following problems arise which are related to the obtainment of user's biological information described in "Background Art".

How program content represented by a TV program (hereinafter, also simply referred to as program) is viewed by a user has been diversified. Objective evaluation for a produced program is an important factor for a TV production company. Specifically, the objective evaluation includes evaluation for the biological information of a user viewing the program content.

Patent Literature 1 (PTL 1) discloses a technique for adding information to a viewing program using user's biological information.

Moreover, Patent Literature 2 (PTL 2) discloses a technique for collecting the biological information of a user without contact with the user, and changing the audio of content being played, according to the collected biological information.

However, PTL 1 requires a dedicated device for obtaining user's biological information. Operations other than viewing are troublesome matters for a viewer viewing program content.

In PTL 2, user's biological information is obtained using a camera.

The environment in which a user at whom a camera is aimed is viewing a program is different from the usual environment in which the user is viewing a program in a relaxed state. Thus, using the obtained biological information is not preferable. Moreover, there is the limitation that the user has to view the program in the imaging area of the camera.

Furthermore, in PTL 2, the audio information of content to be played changes according to the obtained user's biological information.

The content which the user views changes every time. Content to be played is different for each user. Therefore, even if user's biological information is collected for different programs, an accurate evaluation result cannot be obtained for program content.

Moreover, a program time (a period of time during which a program is broadcasted or played) differs depending on the program. Meanwhile, the user using the relaxation equipment enters a relaxed state or an un-relaxed state according to the surrounding environment of the user which is prepared by the relaxation equipment. Thus, in some cases, a user who views a program while using relaxation equipment finishes viewing a program without being relaxed, depending on the program.

In view of the above problems, the present invention provides a method of controlling relaxation equipment for relaxing the user along with the progress of a program. This means that the object of the present invention is to provide a viewing system and a viewing method which can prepare the environment in which the user can view program content in a relaxed state and generate viewing information including biological information for program content.

To solve such problems, a method of controlling relaxation equipment according to one aspect of the present invention is a method of controlling relaxation equipment capable of changing a biological value of a user. The method includes: obtaining a user model including a transition in biological value within a period from a start time to an end time of a program; obtaining a first biological value of the user viewing the program; and controlling the relaxation equipment such that the biological value of the user at the end time approximates a second biological value included in the user model, which is a value at the end time, based on the first biological value and the second biological value.

According to this, the relaxation equipment is controlled such that the biological value of the user at the end time of the program approximates the biological value included in the user model. When the user model represents a transition in the biological value of the user who can relax during the program, the relaxation equipment is controlled such that the level of relax which the user feels during the program increases and the user finishes viewing a program and using the relaxation equipment in a relaxed state. Thus, the method of controlling can relax the user along with the progress of the program.

For example, in the controlling, the relaxation equipment is further controlled such that the biological value of the user at a predetermined time during the program approximates a third biological value included in the user model, which is a value at the predetermined time, based on the first biological value and the third biological value.

According to this, the relaxation equipment is controlled such that the transition in the biological value of the user during the program approximates the transition in biological value included in the user model. Thus, the method of controlling can relax the user along with the progress of the program.

For example, the method of controlling relaxation equipment further includes displaying the first biological value and a transition in the biological value of the user which is predicted from the first biological value and the transition included in the obtained user model.

According to this, the relaxation equipment displays the obtained biological value of the user and the predicted transition in the biological value of the user. Checking the displayed biological value and its transition not only enables the user to check her or his own biological value, but also enables a person other than the user to check the biological value of the user.

For example, the method of controlling relaxation equipment further includes controlling electrical equipment in a home where the relaxation equipment is placed such that the biological value of the user gradually changes after the program ends.

According to this, the relaxation equipment gradually changes the biological value of the user who finished using the relaxation equipment, by controlling electrical equipment in a home where the relaxation equipment is placed. This can reduce the physical burden of the user who finished using the relaxation equipment.

For example, the relaxation equipment includes a bathtub which the user is able to get into.

According to this, the user can relax by getting into the bathtub, which is the relaxation equipment, i.e., by taking a bath in the relaxation equipment.

For example, the biological value is a heart rate, and in the controlling, the relaxation equipment is controlled by controlling a temperature of hot water in the bathtub.

According to this, the relaxation equipment controls the temperature of hot water in the bathtub, which is the relaxation equipment. Here, the heart rate of the user is used as the biological value of the user. That is, the relaxation equipment can relax the user who takes a bath while viewing a program, based on the transition in heart rate included in a user model and the obtained heart rate of the user.

For example, in the controlling, when the heart rate of the user at the end time is lower than the second biological value, based on an assumption that the heart rate of the user after the first biological value is obtained transitions from the first biological value in a same way as a heart rate in the user model transitions, the relaxation equipment is controlled by increasing the temperature of hot water in the bathtub.

According to this, specifically, the temperature of hot water in the bathtub, which is the relaxation equipment, can be controlled based on the heart rate of the user.

Moreover, a method of creating a user model, according to one aspect of the present invention includes: obtaining, from an external server, program information including a start time and an end time of a program; extracting, from the obtained program information, the start time and the end time of the program, to obtain biological values of users with relaxation equipment within a period from the start time to the end time of the program; and creating a user model by performing statistical processing on transitions in the obtained biological values, depending on the program information.

According to this, a user model is created by performing statistical processing on the biological values of the users who used the actual relaxation equipment, in view of information on the program(s) which the users viewed (program information). Here, the biological values of the users are the biological values of the users who, in fact, used the relaxation equipment while viewing the programs. Many of the users were probably in a relaxed state during the program(s). Therefore, the user model created as described above can relax a user during a program when relaxation equipment is controlled based on the transition in biological value in the user model. Therefore, a user model which can relax a user along with the progress of the program is created by the method of creating.

For example, the program information includes program identification information for identifying the program, and in the creating, the user model is created by performing the statistical processing on the transitions in the obtained biological values, on a program basis.

According to this, when creating the user model, the statistical processing is performed on the biological values of the users on a program basis. That is, since the statistical processing is performed on the biological values of the users who viewed the same program, a more accurate user model is created.

For example, the program information includes genre identification information for identifying a genre of the program, and in the creating, the user model is created by performing the statistical processing on the transitions in the obtained biological values, on a genre basis.

According to this, when creating the user model, the statistical processing is performed on the biological values of the users on a program genre basis. That is, since the statistical processing is performed on the biological values of the users who viewed programs belonging to the same genre, a more accurate user model is created.

For example, in the creating, the user model is updated by creating a new user model every time the biological values of the users are obtained in the extracting.

According to this, when the biological values of the users who used the relaxation equipment while viewing a program (programs) are newly obtained, a new user model is created in view of the obtained biological values.

Moreover, a method of managing relaxation equipment according to one aspect of the present invention is a method of managing relaxation equipment capable of changing a biological value of a user. The method includes: the method of controlling relaxation equipment described above; and the method of creating a user model described above, in which in the obtaining of the user model in the method of controlling the relaxation equipment, a user model created by the method of creating a user model is obtained as the user model.

According to this, the relaxation equipment is controlled using the user model created as described above. Therefore, the user can relax along with the progress of the program.

Moreover, a control system of relaxation equipment according to one aspect of the present invention is a control system of relaxation equipment capable of changing a biological value of a user. The control system includes: a model obtainment unit which obtains a user model including a transition in biological value within a period from a start time to an end time of a program; a biological information obtainment unit which obtains a first biological value of a user viewing the program; and a control unit which controls the relaxation equipment such that the biological value of the user at the end time approximates the second biological value included in the user model, which is a value at the end time, based on the first biological value and the second biological value.

According to this, effects similar to the effects in the method of controlling relaxation equipment described above can be obtained.

It should be noted that general and specific aspect(s) disclosed above may be implemented using a system, a method, an integrated circuit, a computer program, or a computer-readable recording medium such as a CD-ROM, or any combination of systems, methods, integrated circuits, computer programs, or computer-readable recording media.

The following specifically describes embodiments with reference to drawings.

It should be noted that each of the embodiments described below shows a general or specific example. Numerical values, shapes, materials, structural elements, the arrangement and connection of the structural elements, steps, the order of steps, and others indicated in the following embodiments are mere examples, and are not intended to limit the present invention. Among the structural elements in the following embodiments, the structural elements not recited in the independent claims representing superordinate concept are described as arbitrary structural elements Embodiment 1

With reference to the drawings, the following describes the control system of relaxation equipment (hereinafter, simply referred to as "control system"), the method of controlling the relaxation equipment (hereinafter, simply referred to as "controlling method"), and the method of creating a user model, which are aspects of the present embodiment. The present embodiment shows examples of the control system and the controlling method used when a user views program content in a relaxed state in a bathtub in a bathroom.

FIG. 1 is a network chart illustrating an example of a control system in the present embodiment.

As FIG. 1 illustrates, a control system 1 includes a viewing information management server 100, relaxation equipment 103, a program information management server 106, and a receiver 107. These devices and servers can mutually communicate via a communication network 105 such as the Internet or an intranet. That is, the relaxation equipment 103 can communicate with the viewing information management server 100 via the communication network 105. Moreover, the program information management server 106 and the receiver 107 can communicate with the viewing information management server 100 via the communication network 105.

The relaxation equipment 103 is a device for relaxing a user. The user can relax by using the relaxation equipment 103. Moreover, the relaxation equipment 103 transmits its setting information to the viewing information management server 100. The relaxation equipment 103 is, for example, a bathtub in a bathroom. In this case, the user relaxes during half-body bathing or full-body bathing in the bathtub. Moreover, the setting information is the temperature of hot water (temperature of hot water in the bathtub). Furthermore, the setting information may include the temperature of the bathroom. It should be noted that a mist sauna or a massage chair can be another example of the relaxation equipment.

The relaxation equipment 103 includes a biological information obtainment unit 104.

The biological information obtainment unit 104 obtains biological information from the user using the relaxation equipment 103, and transmits the obtained biological information to the viewing information management server 100. The biological information includes a biological value measured from a living body and time. A specific example of the biological value is a heart rate. When a bathtub is used as the relaxation equipment, a heart rate measuring device, a scale, or others can be used as a sensor for collecting the biological information. The biological information obtainment unit 104 obtains, as the biological information, the heart rate of the user viewing a program, together with time (time when the biological information is obtained). Specifically, given that the user is viewing the program at 8 pm and the heart rate of the user at this time is 60 beats per minute, the biological information obtainment unit 104 associates and records "8 pm", which is the time when the biological information is obtained, and "heart rate: 60", which is the biological value. Moreover, the biological information obtainment unit 104 transmits the obtained biological information to the viewing information management server 100.

It should be noted that another example of the biological value includes weight, perspiration, or body temperature which can be obtained by the sensor. Moreover, the obtained biological value may be quantified as, for example, "excitement" or "no reaction", based on a change in heart rate.

The receiver 107 displays a program. The user views a program displayed by the receiver 107 while using the relaxation equipment 103. The receiver 107 is, for example, a television receiver (TV) having a waterproofing function. Moreover, the receiver 107 plays a program currently on the air or a recorded program.

The receiver 107 includes an operation information obtainment unit 108.

The operation information obtainment unit 108 obtains operation information on operation performed by the user on the receiver 107, together with the time when the operation is performed (operation time). The operation information obtainment unit 108 then transmits the obtained operation information and time to the viewing information management server 100. The operation information obtainment unit 108 is, for example, a remote control for operating the receiver 107. The operation information indicates the selection of a TV viewing channel or the playback, stop, fast forward, or rewind of a recorded program. The operation information obtainment unit 108 obtains the information from the remote control operation performed by the user.

The viewing information management server 100 obtains the biological information from the relaxation equipment 103, obtains the program information from the program information management server 106, and obtains the operation information from the receiver 107. The viewing information management server 100 can communicate with more than one relaxation equipment 103 via the communication network 105.

The viewing information management server 100 includes a viewing information generation unit 101, a data storage unit 102, and a data analysis unit 109.

The viewing information generation unit 101 generates program information including biological information from (i) the biological information received from the relaxation equipment 103, (ii) the program information on a program being viewed by the user, obtained from the program information management server 106, and (iii) the operation information received from the receiver 107.

The program information is, for example, data representing date and time when a program was broadcasted or time (broadcast time), the title of the program, the genre of the program, and the cast.

Program information on a program the broadcasting of which has already ended includes, in addition to the above program information, a keyword on a program scene basis.

In the program information including biological information, the broadcasted program or the recorded and played back program are associated with biological information, based on, for example, the time when the program was broadcasted included in the program information, the time when the biological information was obtained included in the obtained biological information, and the time when the operation was performed included in the operation information. As a result, biological information on a scene in the program is recorded as the program information.

The data storage unit 102 stores the generated program information including biological information in a recording device (not illustrated in the figure). The data storage unit 102 stores the program information including biological information in, for example, a hard disk in the data storage unit 102.

The data analysis unit 109 generates a user model from the stored program information including biological information. A vast amount of program information including biological information may be stored. That is, the data analysis unit 109 may receive the program information including biological information generated based on pieces of the biological information of many users. The data analysis unit 109 generates the user model by, for example, performing statistical processing on the stored program information including biological information. It should be noted that the statistical processing is, for example, averaging processing (calculating the average value of values).

Figure 2A:
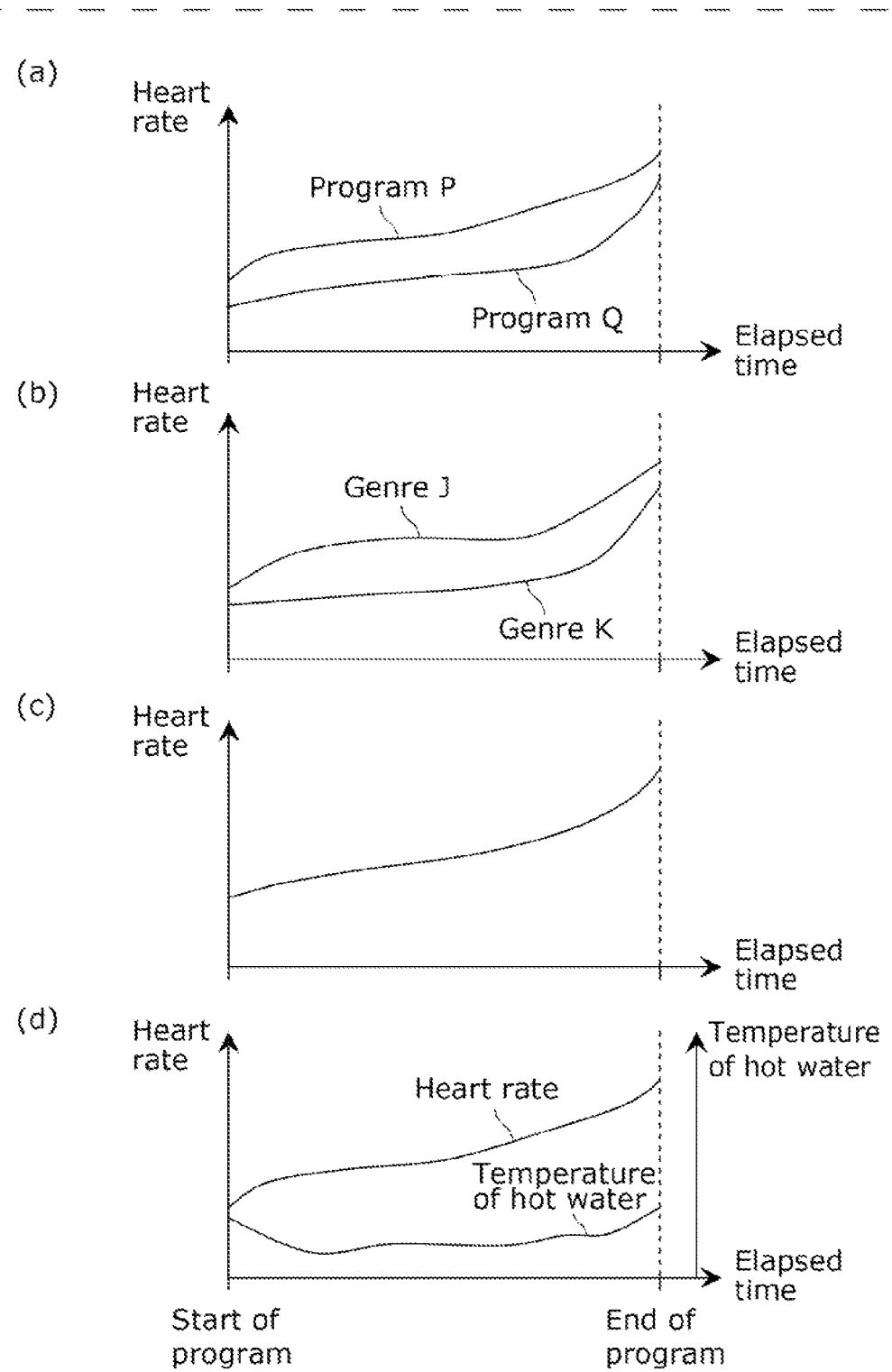
FIG. 2A is a figure for explaining user models in Embodiment 1.

With reference to FIG. 2A, the following describes user models. FIG. 2A is a figure for explaining user models in the present embodiment. There are various kinds of user models, for example, as described below.

1. A user model calculated by performing, for each program, the statistical processing on the given biological values of users (the average value model of biological values for each program) ((a) in FIG. 2A).

2. A user model calculated by categorizing programs according to the genre, and performing, for each genre, the statistical processing on the given biological values of users (the average value model of biological values for each genre) ((b) in FIG. 2A).

3. A user model calculated by performing, across all the programs, the statistical processing on the given biological values of users (the average value model of biological values across all the programs) ((c) in FIG. 2A).

4. A user model obtained by extracting the relationship between (i) a change in setting information of the relaxation equipment when a user is viewing a program (the temperature of a bathroom and the temperature of hot water in a bathtub) as the play time elapses and (ii) a change in the biological value of the user as the play time elapses ((d) in FIG. 2A).

5. A user model obtained by categorizing users who viewed the same program into more than one user group, based on a predetermined condition, and extracting the features of biological values for each user group (equivalent to a model obtained by generating (d) in FIG. 2A for each user group).

In the above, the statistical processing in a user model is processing for calculating, for each time, the average value of the biological values of users which change with the lapse of time.

Here, the following specifically describes the first to fifth user models.

The first user model is calculated as a value obtained by averaging, for each time, the biological values of more than one use in program information including pieces of biological information of the users generated for one program.

The second user model is calculated as a value obtained by averaging, for at least one program and for each time, the biological values of more than one user in program information including pieces of biological information of the users generated for at least one program belonging to one genre. This means that the second user model is calculated as a value obtained by averaging, for at least one program and for each time, the first user model calculated for at least one program belonging to one genre.

In the second user model, for example, when a program belongs to the genre of "period drama", heart rate peaks in the last ten minutes during the program.

The third user model is calculated as a value obtained by averaging, for each time, the biological values of all the users in program information including pieces of biological information of all the users generated for all the programs. The third user model represents a value, which varies as time elapses, of the heart rate of a user using a bathtub during, for example, half-body bathing. Here, such value is estimated from a change in the heart rate with the lapse of time, i.e., for the length of the play time of stored program content.

The fourth user model is obtained by associating program information on a viewed program and changes, with the lapse of time, in the temperature of a bathroom and the temperature of hot water in a bathtub. Here, the bathroom and bathtub were used by the user viewing the program. That is, in the fourth user model, a change in heart rate is associated with the changes in the temperature of the bathroom and the temperature of hot water in the bathtub.

The fifth user model is obtained by categorizing users having program preferences similar to those of the user into the same group (user group), based on the viewing histories of the users, and extracting the features of the biological values of the users belonging to the group.

It should be noted that the larger the amount of program information including biological information on many users the data storage unit 102 collects, the better the accuracy of the user model is. Here, the collected program information including biological information may be obtained by the relaxation equipment controlled by the control system as described in Embodiment 2 or may be obtained by the relaxation equipment controlled by a user according to the preferences of the user. Thus, a user model with relatively high accuracy is created by performing the statistical processing on the results of various controls performed by various users.

It should be noted that stored program information including biological information is transmitted to an institution and a corporation which evaluate a program, such as a TV production company.

The following describes the operation of the viewing system configured as above.

Figure 2B:
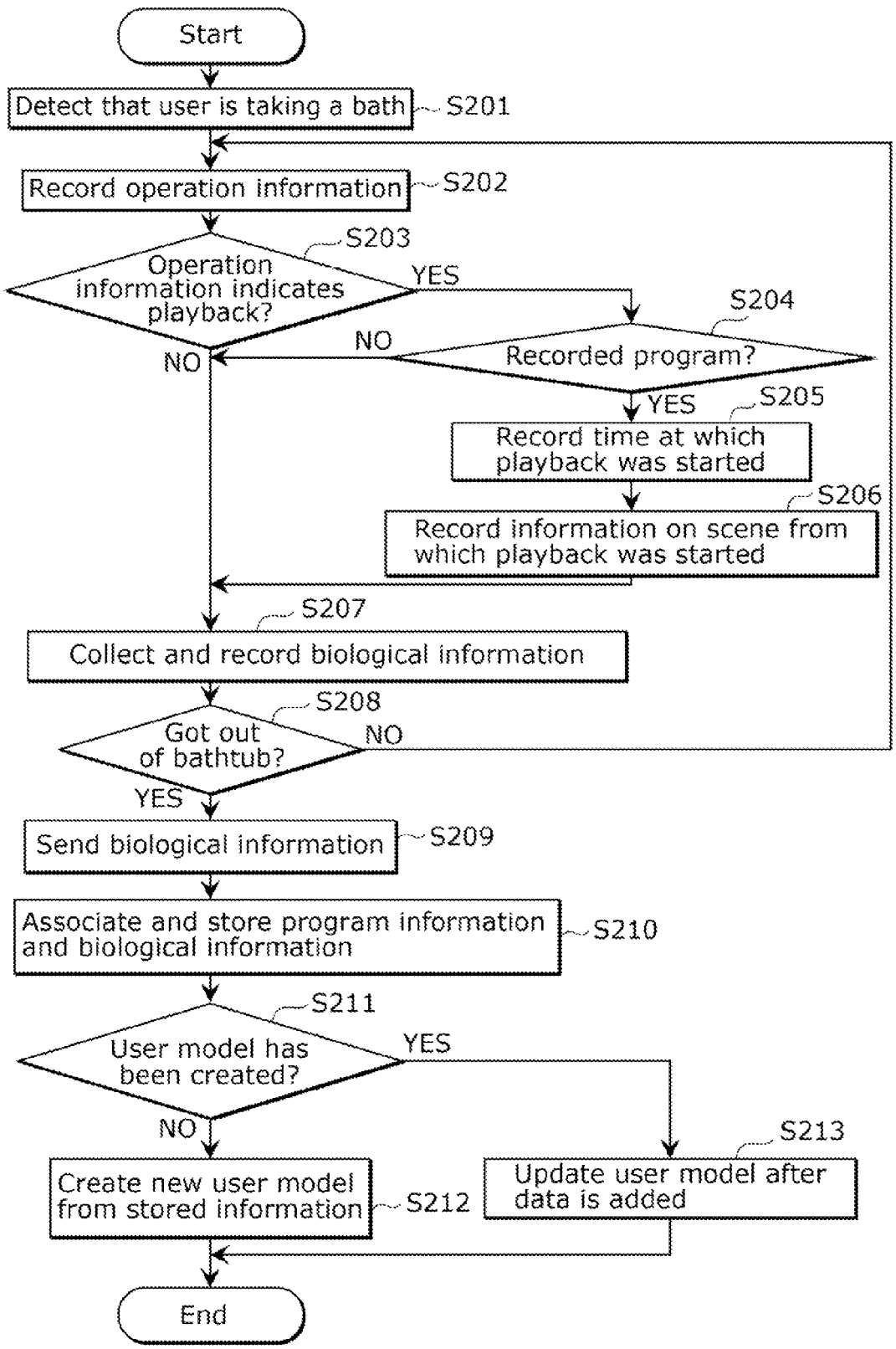
FIG. 2B is a flowchart illustrating an example of the operation of a control system in Embodiment 1.

FIG. 2B is a flowchart illustrating an example of the operation of the control system in the present embodiment.

In step S201, the biological information obtainment unit 104 of the relaxation equipment 103 detects that the user started using the relaxation equipment. More specifically, the biological information obtainment unit 104 detects that the user started taking a bath, from a detected value or a change in the detected value in a scale or a heart rate sensor, which is the biological information obtainment unit 104 of the relaxation equipment 103.

In step S202, the operation information obtainment unit 108 obtains operation information based on operation performed by the user on the receiver 107, and records the obtained operation information. Moreover, the operation information obtainment unit 108 transmits the recorded operation information to the viewing information management server 100. It should be noted that the operation information obtained by the operation information obtainment unit 108 may be temporarily recorded by the receiver 107, and then transmitted to the viewing information management server 100 by the receiver 107.

In step S203, the viewing information management server 100 determines whether or not the received operation information is a "play" operation. When the operation performed by the user on the receiver 107 is not "play" (NO in step S203), step S207 is performed. The procedure goes on to the next processing of collecting and recording biological information (processing other than play in S203).

Meanwhile, when the operation performed by the user on the receiver 107 is "play" operation (YES in step S203), the viewing information management server 100 determines whether the played program is a recorded program or a broadcast program currently on the air, in step S204. Specifically, the viewing information management server 100 determines whether the played content is the recorded program or broadcast content, based on the program information obtained from the program information management server 106 and the operation information received from the receiver 107.

When the played content is the recorded program (YES in step S204), the viewing information management server 100 records the start time of playback of the content in step S205.

In step S206, the viewing information management server 100 identifies scene information on the scene from which the playback was started, based on the time when the playback was started, using the program information, and records the identified scene information.

Meanwhile, when the played program is not the recorded program (that is, the played program is the broadcast program), the viewing information management server 100 identifies, in step S221, a program currently on the air from the current time and the program information obtained from the program information management server 106.

In step S207, after the play of the program is started, the relaxation equipment 103 collects the biological information of the user, and records the collected biological information. Specifically, the biological information obtainment unit 104 of the relaxation equipment 103 obtains the biological information, and records the obtained biological information together with the time when the biological information was obtained (biological-information obtained time). It should be noted that the biological information may be temporarily recorded on the relaxation equipment 103, or may be transmitted to the viewing information management server 100 every time the biological information is collected.

In step S208, during the play of the program, the biological information obtainment unit 104 of the relaxation equipment 103 regularly collects and records the biological information of the user, and determines whether or not the user is out of the bathtub. It should be noted that the biological information obtainment unit 104 may collect the biological information at any timing. However, the accuracy of the biological information for the program improves when the information is obtained at shorter intervals.

In step S208, when the biological information obtainment unit 104 determines that the user is not out of the bathtub (NO in step S208), the procedure goes back to step S202. It should be noted that in step S202, it may be found that the user is playing a new program different from the program which the user has viewed so far, based on the operation information obtained by the operation information obtainment unit 108.

Meanwhile, when the biological information obtainment unit 104 of the relaxation equipment 103 determines that the user is out of the bathtub (YES in step S208), the biological information temporarily recorded on the relaxation equipment 103 is transmitted to the viewing information management server, in step S209.

In step S210, the viewing information management server 100 receives the biological information from the relaxation equipment 103. The viewing information generation unit 101 of the viewing information management server 100 generates program information including biological information by associating program information and the biological information with reference to the biological-information obtained time, broadcasted time, and operated time included in the biological information obtained from the relaxation equipment 103, program information obtained from the program information management server 106, and operation information obtained from the receiver 107, respectively, using the biological information, the program information, and the operation information.

The data storage unit 102 stores the generated program information including biological information in the recording device of the viewing information management server 100. Specifically, the program information including biological information is stored by writing into a database.

The data analysis unit 109 creates a user model from the stored program information including pieces of biological information. Specifically, the data analysis unit 109, for example, calculates, using the program information including pieces of biological information, the average value of changes in the heart rates of users using the relaxation equipment 103, for the program which the users are viewing. The following describes the processing in which the data analysis unit 109 creates a user model from the stored program information including pieces of biological information.

In step S211, the data analysis unit 109 determines whether or not the user model has been created for a viewed program.

When determining that the user model has not been created for the viewed program in step S211 (NO in step S211), the data analysis unit 109 creates a new user model in step S212. Specifically, the data analysis unit 109 registers, in a database, the program information including biological information created in step S210, and creates a user model based on the registered program information including biological information.

When determining that the user model has been created for the viewed program in step S211 (YES in step S211), the data analysis unit 109 updates the user model in step S213. Specifically, the data analysis unit 109 adds to the database, as a difference, the program information including biological information created in step S210, and updates the user model based on the added program information including biological information.

The above steps enable the collection of the biological information of a user viewing a program, with relaxation equipment represented by a bathtub, the addition of the collected biological information to the program information, and the creation of information usable in the objective evaluation of user's reaction for the program.

Thus, according to the method of creating a user model in the present embodiment, a user model is created by performing the statistical processing on the biological values of the users who used actual relaxation equipment, in view of information on the program(s) which the users viewed (program information). Here, the biological values of the users described above are obtained from the users who, in fact, used the relaxation equipment while viewing the program. Many of the users were probably in a relaxed state during the program. Therefore, the user model created as described above can relax a user during the program by controlling relaxation equipment based on a transition in biological value in the user model. Therefore, the user model which can relax users along with the progress of a program is created by the method of creating a user model.

Moreover, when creating the user model, the statistical processing is performed on the biological values of users on a program basis. That is, the statistical processing is performed on the biological values of the users who viewed the same program. This creates a more accurate user model.

Moreover, when creating the user model, the statistical processing is performed on the biological values of the users on a program genre basis. That is, the statistical processing is performed on the biological values of the users who viewed programs belonging to the same genre. This creates a more accurate user model.

Moreover, when the biological value of a user who used relaxation equipment while viewing a program is newly obtained, a new user model in view of the obtained biological values is created.

Moreover, relaxation equipment is controlled using a user model created as described above. Therefore, users can relax along with the progress of the program.

Embodiment 2

Figure 3:
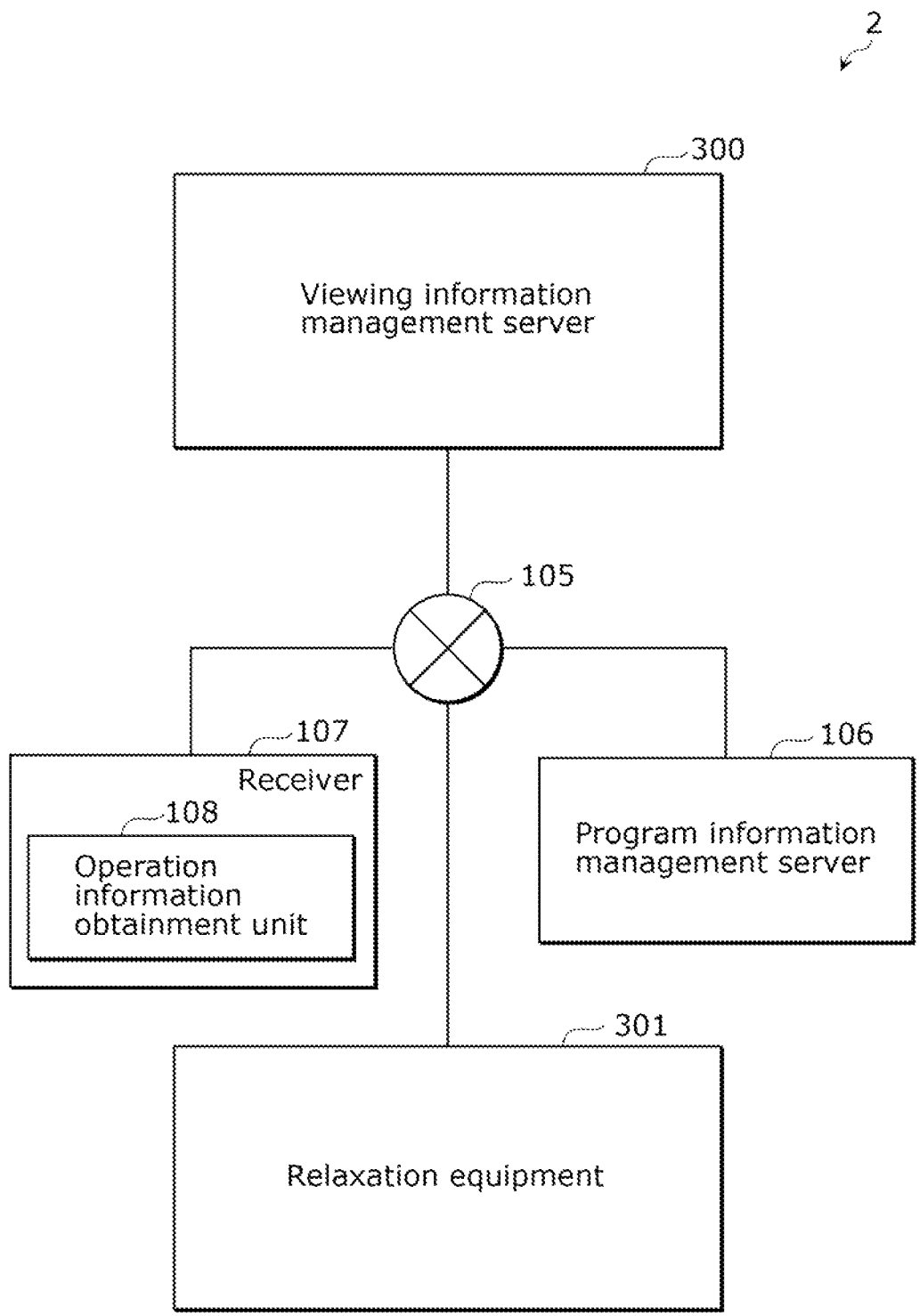
FIG. 3 is a network chart illustrating an example of a control system in Embodiment 2.

FIG. 3 is a network chart illustrating an example of a control system in the present embodiment.

As illustrated in FIG. 3, a control system 2 includes a viewing information management server 300, relaxation equipment 301, a program information management server 106, and a receiver 107. These devices and servers can mutually communicate via a communication network 105 such as the Internet or an intranet. That is, the relaxation equipment 301 can communicate with the viewing information management server 300 via the communication network 105 such as the Internet or an intranet.

Here, the following example is based on the assumption that the relaxation equipment 301 is a bathroom or a bathtub. It should be noted that the relaxation equipment 301 is not limited to the bathroom and the bathtub, but may be a massage chair or a mist sauna.

The configurations and operations of the program information management server 106, the receiver 107, and the operation information obtainment unit 108 are similar to those in Embodiment 1. Therefore, the explanation for these configurations and operations will be omitted.

A user views a program with the receiver 107 while using the relaxation equipment 301.

The relaxation equipment 301 obtains the biological information of the user viewing the program, and transmits the biological information to the viewing information management server 300.

The viewing information management server 300 generates program information including biological information, using the biological information obtained from the relaxation equipment 301, program information obtained from the program information management server 106, and operation information obtained from the receiver 107. The viewing information management server 300 then stores the created program information. Moreover, the viewing information management server 300 creates control information for the relaxation equipment 301, based on the stored program information including biological information, and transmits the created control information to the relaxation equipment 301. The details of the control information will be described later.

The relaxation equipment 301 changes the settings of the relaxation equipment 301 based on the control information received from the viewing information management server 300, and provides the environment in which the user can view a program in a relaxed state. The settings of the relaxation equipment 301 include, for example, the temperature setting of a bathtub. The relaxation equipment 301 prevents the user from feeling dizzy or a chill while viewing a program in the bath by controlling a setting temperature in the bathtub.

Figure 4:
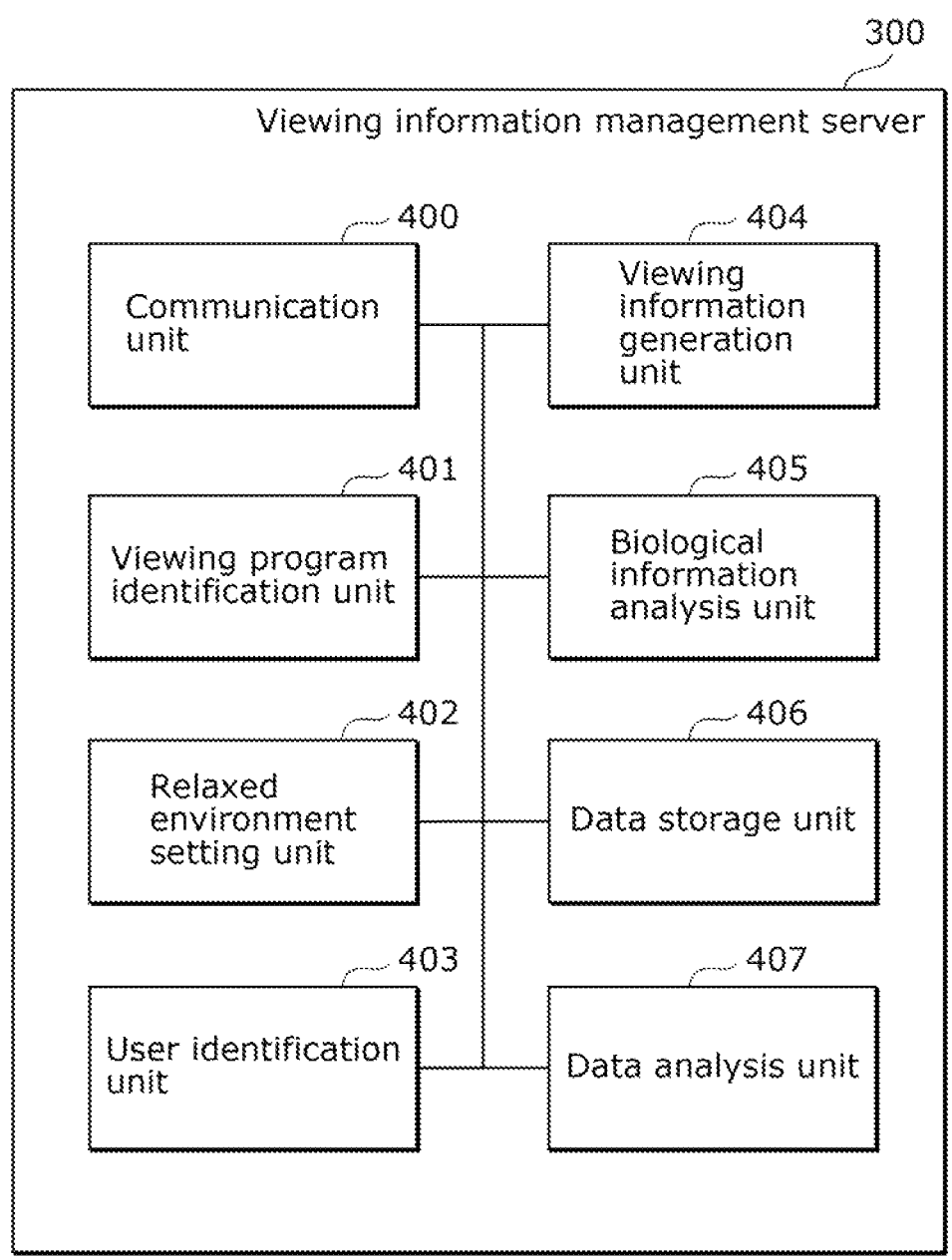
FIG. 4 is a block diagram illustrating an example of a viewing information management server in Embodiment 2.

With reference to FIG. 4, the following describes the configuration of the viewing information management server 300.

FIG. 4 is a block diagram illustrating an example of a viewing information management server in the present embodiment.

As illustrated in FIG. 4, the viewing information management server 300 includes a communication unit 400, a viewing program identification unit 401, a relaxed environment setting unit 402, a user identification unit 403, a viewing information generation unit 404, a biological information analysis unit 405, a data storage unit 406, and a data analysis unit 407.

The communication unit 400 is connected to the communication network 105 through which the communication unit 400 is connected to the relaxation equipment 301, the receiver 107, the program information management server 106, and a world wide web (WWW) (not illustrated in the figure), to transmit and receive data. The communication unit 400 is, for example, a communication interface such as a wire local area network (LAN) or a wireless LAN.

The biological information analysis unit 405 analyzes the biological information of the user obtained from the relaxation equipment 301. The biological information includes a biological value measured from a living body and time. As with Embodiment 1, a specific example of the biological value is the heart rate (heart rate which changes with the lapse of time) of a user viewing a program.

The biological information analysis unit 405 determines whether or not the heart rate of the user is an abnormal value. Moreover, the biological information analysis unit 405 quantifies user's reaction for the program, such as excitement or calm, based on a change in heart rate.

The user identification unit 403 identifies the user from the biological information (biological value) obtained from the relaxation equipment 301. The biological information (biological value) used for identifying a user is, for example, weight. That is, the user identification unit 403 identifies the user by comparing the preregistered weight of the user and a weight obtained from the relaxation equipment 301. It should be noted that the biological information (biological value) for identifying the user may be the average heart rate of the user. Here, the user identification unit 403 may collect the weight and the average heart rate of the user which need to be preregistered, from other devices such as a scale and a heart rate meter, and store the collected weight and average heart rate. It should be noted that the user identification unit 403 can identify the user from a change in water level in a bathtub when the user gets into the bathtub.

The viewing program identification unit 401 identifies the program which the user is viewing while using the relaxation equipment 301, based on program information obtained from the program information management server 106 and operation information obtained from the receiver 107. The viewing program identification unit 401, for example, identifies a program currently on the air, based on a selected channel included in the operation information and time information. Moreover, when the operation information indicates the playback of the recorded program, the viewing program identification unit 401 identifies, from the program information, the title of the played back program and the scene from which the playback was started.

The viewing information generation unit 404 generates program information including biological information by associating, based on time, the obtained biological information and program information.

The data storage unit 406 stores the generated program information including biological information in a recording device (not illustrated in the figure). For example, to store the program information including biological information in the data storage unit 406 is to record the information in the recording device such as a hard disk. Moreover, the program information including biological information is preserved in an accessible database.

The data analysis unit 407 extracts, from the stored program information including biological information, a user model representing the tendency of a change with the lapse of time in user's biological information for a program. It should be noted that an example of the user model is one of the user models described in Embodiment 1.

The relaxed environment setting unit 402 determines the setting value of the relaxation equipment 301 from the program information and the stored program information including biological information. The relaxed environment setting unit 402 predicts a change in heart rate by obtaining a coefficient representing (i) the relationship between the time length of the program and a change in the temperature of hot water in the bathtub where the user is taking a bath and (ii) the relationship between the time length of the program and a change in the heart rate of the user viewing the program. The coefficient is obtained using the fourth user model (described in Embodiment 1) generated from the stored program information including biological information. The relaxed environment setting unit 402 adjusts temperature such that the user would like to get out of the bathtub around the time when the program which the user is viewing ends. The relaxed environment setting unit 402 is equivalent to a model obtainment unit and a control unit.

Such control performed by the relaxed environment setting unit 402 allows the user to view the program in a relaxed state until the end of the program, without feeling dizzy when taking a bath. Therefore, the biological information of the user viewing the program is obtained for the entire time of the program. This can create program information which can be referenced by a third-party institution when evaluating the program.

Figure 5:
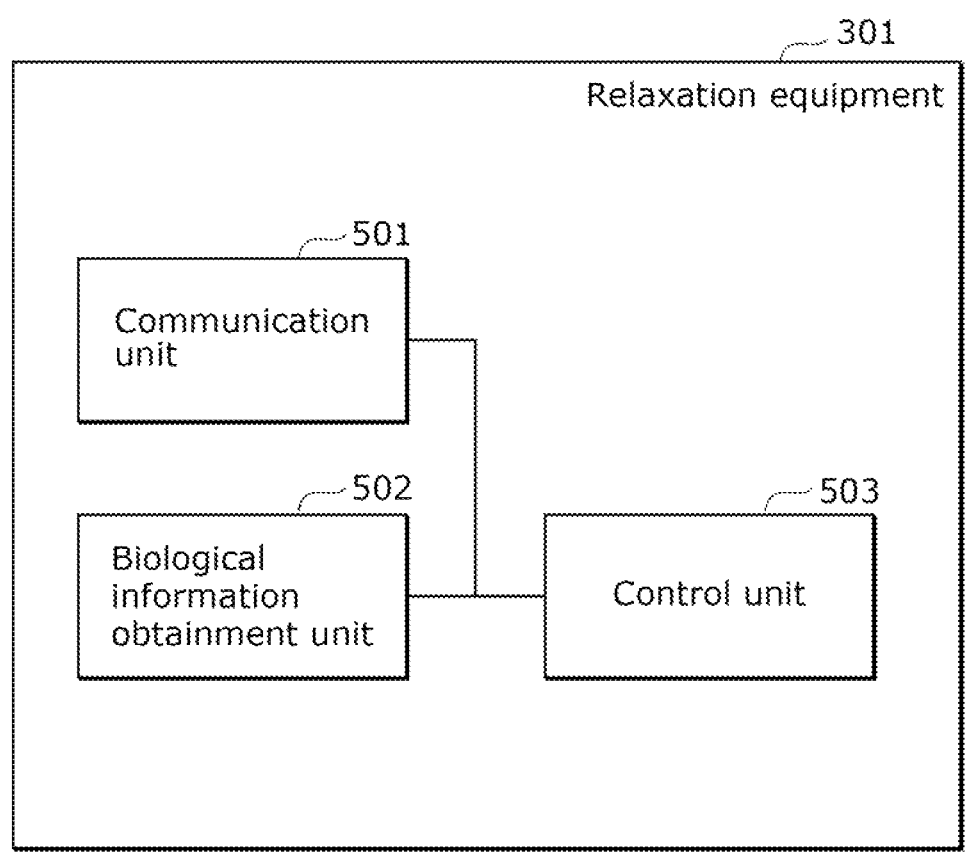
FIG. 5 is a block diagram illustrating an example of relaxation equipment in Embodiment 2.

With reference to FIG. 5, the following describes the configuration of the relaxation equipment 301.

FIG. 5 is a block diagram illustrating an example of relaxation equipment in the present embodiment.

As illustrated in FIG. 5, the relaxation equipment 301 includes a communication unit 501, a biological information obtainment unit 502, and a control unit 503.

The communication unit 501 is connected to a communication network through which the communication unit 501 is connected to the viewing information management server 300 and a world wide web (WWW), to transmit and receive data. The communication unit 501 is, for example, a communication interface such as a wire local area network (LAN) or a wireless LAN.

The biological information obtainment unit 502 obtains, as biological information, the biological value of a user using the relaxation equipment 301, together with time (biological-information obtained time). The biological value is, for example, the heart rate of the user. Moreover, the biological information obtainment unit 502 obtains the weight of the user to identify the user.

The control unit 503 controls a function for setting the relaxation equipment 301 and the function of the relaxation equipment 301, based on control information transmitted from the viewing information management server 300. Here, the control information transmitted from the viewing information management server 300 is a setting value for a parameter which can be set for the relaxation equipment 301. When the relaxation equipment 301 is a bathtub, the parameter is "the temperature of hot water in the bathtub", and the setting value is a numeral value such as "38 degrees Celsius". Moreover, the parameter may be "the temperature of a bathroom", and its setting value may be "28 degrees". Moreover, the function of the relaxation equipment 301 is, for example, the function of a jetted bathtub or the function of jetting bubbles containing oxygen.

When the relaxation equipment 301 is a massage chair, a parameter which can be set for the relaxation equipment 301 is the setting of the strength of massage or operation duration. Moreover, the function which can be set for the relaxation equipment 301 is, for example, the function of preventing legs from being swollen.

Moreover, the control information is a command for the function of the relaxation equipment. Specifically, when the bathtub has the function of a jetted bathtub and the control information obtained from the viewing information management server 300 represents "the start of the jetted bathtub", the function indicated in the control information is "the function of the jetted bathtub", and the command "start".

The viewing information management server 300 and the relaxation equipment 301 of the above configurations can provide the environment in which the user can view a program in a relaxed state.

Figure 6:
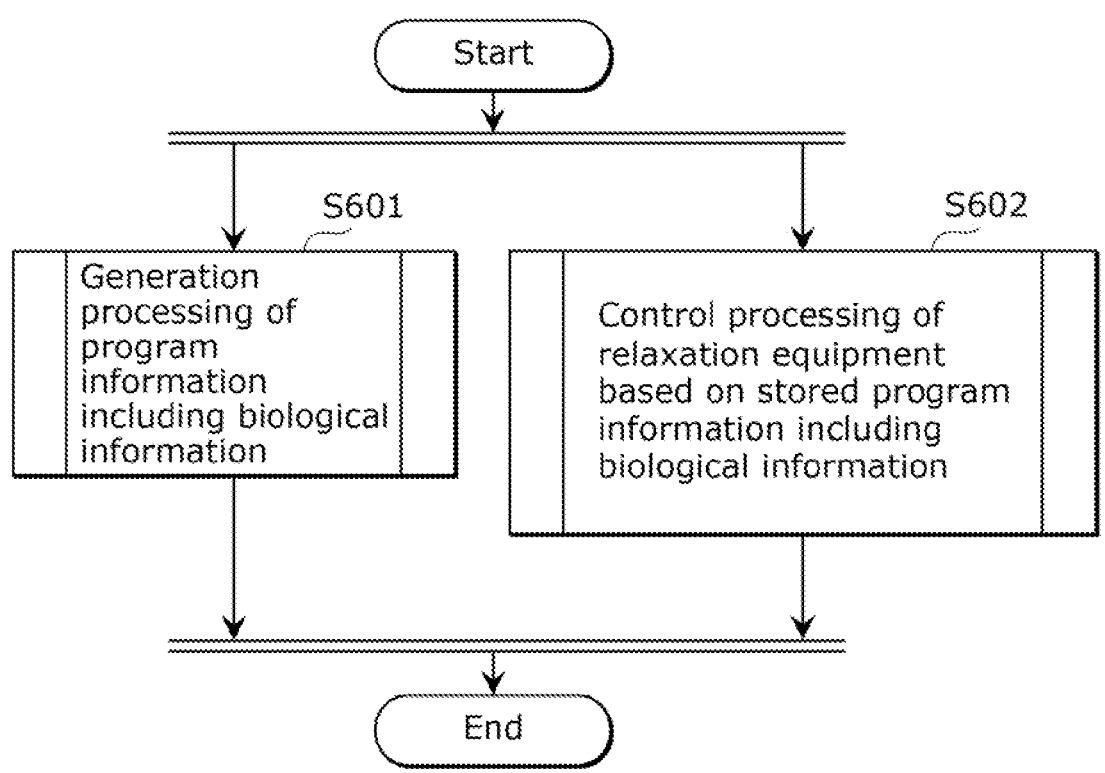
FIG. 6 is a first flowchart illustrating an example of the operation of a control system in Embodiment 2.

FIG. 6 is a first flowchart illustrating an example of the operation of the control system in the present embodiment.

As illustrated in FIG. 6, the control system 2 performs, in parallel, (i) the generation processing of program information including biological information described with reference to FIG. 2B in Embodiment 1 and (ii) the optimization control processing of relaxation equipment based on stored program information including biological information (which will be described later with reference to FIGS. 7, 8A, and 8B).

The generation processing of program information including biological information in step S601 is similar to the processing described with reference to FIG. 2B in Embodiment 1. Therefore, the explanation will be omitted here.

Figure 7:
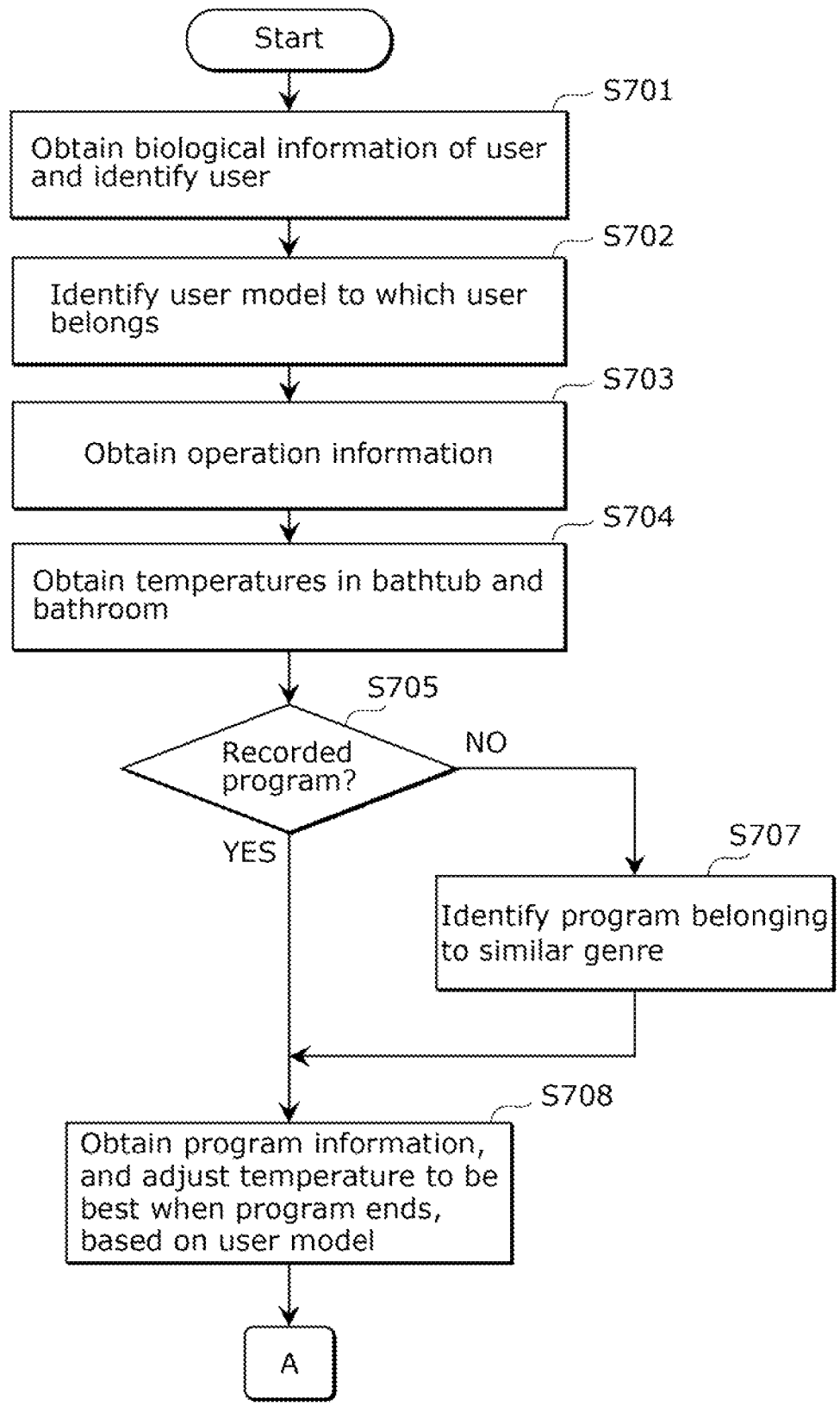
FIG. 7 is a second flowchart illustrating an example of the operation of a control system in Embodiment 2.
Figure 8A:
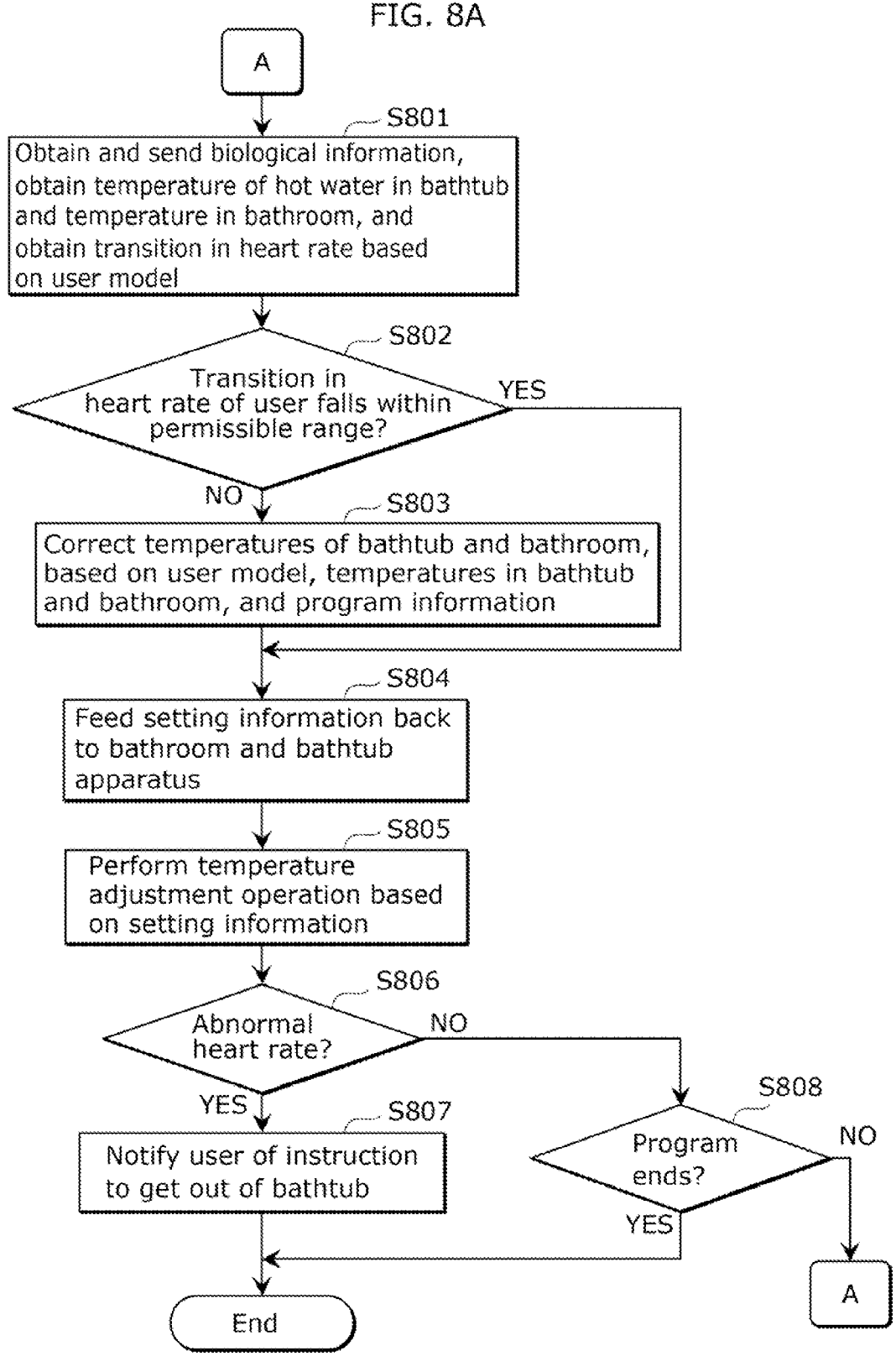
FIG. 8A is a third flowchart illustrating an example of the tri operation of a control system in Embodiment 2.
Figure 8B:
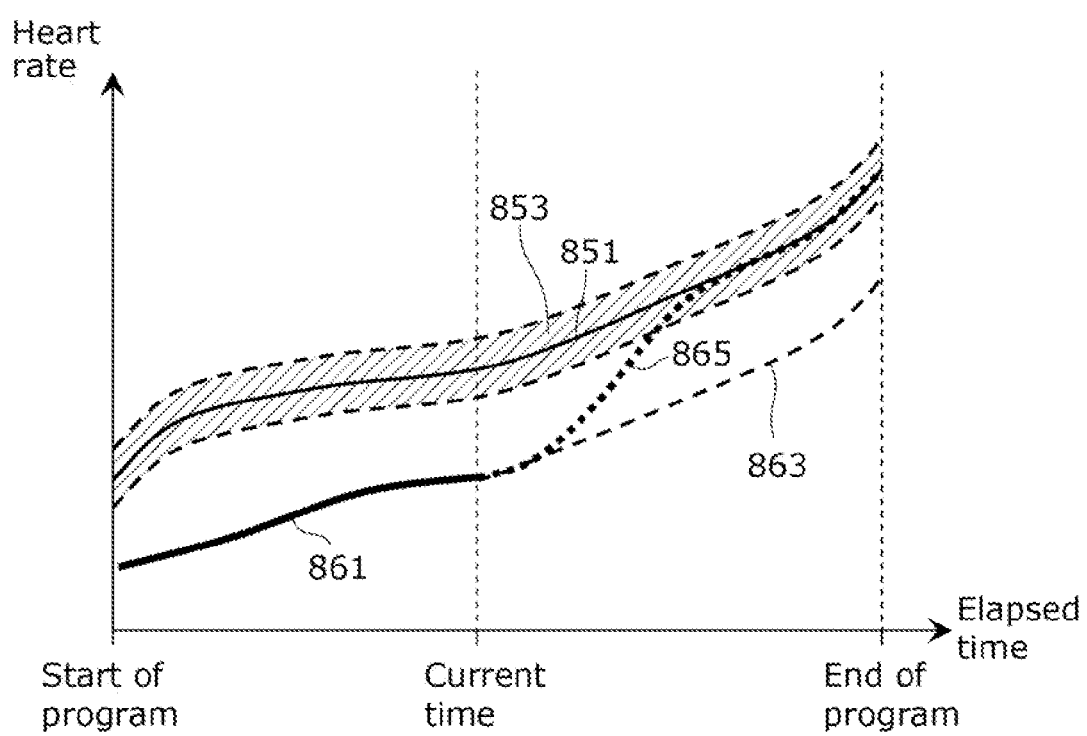
FIG. 8B is a figure for explaining a change in heart rate resulted from control performed by a control system in Embodiment 2.

With reference to FIGS. 7, 8A, and 8B, the following describes the control processing in which the viewing information management server 300 controls the relaxation equipment 301 based on the stored program information including biological information.

FIG. 7 is a second flowchart illustrating an example of the operation of the control system in the present embodiment.

In step S701, the biological information obtainment unit 502 of the relaxation equipment 301 detects a change in weight which is a biological value measured with a scale, and transmits biological information including the detected weight of a user to the viewing information management server 300. The user identification unit 403 of the viewing information management server 300 identifies the user from the received biological information. Here, the user identification unit 403 identifies the user by comparing pre-obtained weight information and obtained weight information.

In step S702, the viewing information management server 300 determines a user model to which the identified user belongs. One of the methods of determining a user model is to identify a group including a user having a history of the programs which the user viewed in the past similar to the history of programs viewed by the user. Moreover, a user model may be determined by identifying, from among created user models, a user model showing a change in biological information which is similar to a change in the biological information of the user viewing the program.

In step S703, the operation information obtainment unit 108 of the receiver 107 obtains operation information on operation performed by the user for a program.

In step S704, the relaxation equipment 301 obtains the setting information of the relaxation equipment 301. When the relaxation equipment 301 is a bathroom or a bathtub, the relaxation equipment 301 obtains the temperatures of the bathroom and the bathtub.

In step S705, the viewing program identification unit 401 determines whether or not a program whose play was started is a recorded program, based on operation information on operation performed by the user on the receiver 107.

When the viewing program identification unit 401 determines that the program whose play was started is a recorded program, based on the operation information on operation performed by the user on the receiver 107 in step S705 (YES in step S705), the relaxed environment setting unit 402 obtains program information including biological information stored by the data storage unit 406 and a user model to which the program being viewed by the user belongs.

In step S708, the relaxed environment setting unit 402 determines the temperature of hot water at which the user is warmed and would like to get out of the bathtub at the timing when the program whose play was started ends.

Meanwhile, when the viewing program identification unit 401 determines that the program whose play was started is not a recorded program (i.e., a program currently on the air is being played), based on the operation information on operation performed by the user on the receiver 107 in step S705 (NO in step S705), programs currently on the air and programs broadcasted in the past are compared to identify a similar program from among the programs currently on the air. Here, the program similar to a program currently on the air is the program which is determined to be similar in the genre, time length, or cast of the program, based on the program information.

By referring to the identified program information and the user model to which the program information belongs, the temperature is adjusted so that the user would like to get out of the bathtub at the timing when the user finishes viewing the program (S708).

Thus, the control system 2 can provide the environment in which the user can view a program without feeling a chill or dizzy even if it is the long program.

FIG. 8A is a third flowchart illustrating an example of the operation of the control system in the present embodiment. FIG. 8B is a figure for explaining a change in heart rate resulted from control performed by a control system in Embodiment 2. With reference to FIG. 8A, the following describes the processing procedure of the viewing system and a transition in the heart rate of the user when the user is viewing program content.

In step S801, the relaxation equipment 301 obtains the heart rate of the user viewing the program, and transmits the obtained heart rate to the viewing information management server 300. Moreover, the relaxation equipment 301 obtains the temperature of hot water in the bathtub and the temperature of the bathroom. The relaxation equipment obtains the transition in the heart rate of the user during the program, which is predicted based on a user model. FIG. 8B illustrates a transition 851 in heart rate in the user model with the lapse of time.

In step S802, the relaxation equipment 301 determines whether or not the heart rate of the user falls within a permissible range, based on the heart rate obtained in step S801 and the predicted transition in heart rate. Specifically, the relaxed environment setting unit 402 calculates a future transition in the heart rate of the user. This calculation is based on the assumption that when the temperature of hot water in the bathtub, the temperature in the bathroom, and the heart rate of the user obtained in step S801 are considered as starting points, the heat rate of the user transitions in the same way as the heart rate in the user model transitions. Whether or not the heart rate at each time represented by the calculated transition in heart rate falls within the permissible range is determined. It should be noted that the permissible range may take a heart rate which is at most 10% higher or lower than the heart rate obtained in step S801. Here, 10% is just an example, and the percentage may be 5% or 20%. FIG. 8B illustrates a transition 863 in heart rate when the above assumption is applied. Moreover, a permissible range 853 is a predetermined range the center of which is the transition 851 in heart rate.

When it is determined that the heart rate of the user does not fall within the permissible range (beyond the permissible range) in step S802 (NO in step S801), the relaxed environment setting unit 402 corrects, in step S803, the temperature of hot water in the bathtub and the temperature of the bathroom, based on a user model showing a change in heart rate which is similar to that of the user. Specifically, the relaxed environment setting unit 402 increases or decreases at least one of the temperature of hot water in the bathtub and the temperature of the bathroom, to control so that the transition in heart rate calculated in step S802 falls within the permissible range, FIG. 8B illustrates a future transition 865 in heart rate when the transition in the heart rate of the user is controlled to fall within the permissible range.

Moreover, the relaxed environment setting unit 402 can perform the following control. The relaxed environment setting unit 402 obtains, from a user model, as the predicted change width of heart rate, the average of changes in the heart rates of users, which represents a change in biological information similar to that of the user. Here, the predicted change width of heart rate is obtained for a scene in a program to be played. The obtained heart rate of the user and the predicted change width of heart rate are added, and the temperature of the bathroom or the temperature of hot water in the bathtub is lowered in advance so that the heart rate will fall within the permissible range in the scene to be played. It should be noted that a change in heart rate based on the stored groups of program information including biological information may be predicted on a program scene basis or on a program basis.

In step S804, the relaxed environment setting unit 402 feeds back by transmitting, to the relaxation equipment 301, the setting information of the temperature of hot water in the bathtub or temperature in the bathroom corrected in step S803.

In step S805, the control unit 503 of the relaxation equipment 301 receives the setting information via the communication unit 400, and controls at least one of the temperature in the bathroom and the temperature of hot water in the bathtub, based on the received setting information. It should be noted that a temperature control for at least one of the temperature in the bathroom and the temperature of hot water in the bathtub are sometimes referred to as "temperature adjustment control".

Subsequently, the control unit 503 continues to perform the temperature control, i.e., the temperature adjustment control for the temperature in the bathroom and the temperature of hot water in the bathtub while the user is viewing program content. The control unit 503 may perform processing subsequent to step S806 while performing the temperature adjustment control.

In step S806, the biological information analysis unit 405 of the viewing information management server 300 monitors the heart rate of the user obtained by the relaxation equipment 301, and determines whether the heart rate reaches an abnormal value. Here, when detecting, based on a user model created from stored program information including biological information, that the obtained heart rate largely departs from the heart rate in the user model (the heart rate is abnormal), the biological information analysis unit 405 determines that the obtained heart rate is an abnormal heart rate.

When the biological information analysis unit 405 determines that the heart rate is abnormal in step S806 (YES in step S806), the viewing information management server 300 transmits, to the relaxation equipment 301, the notification for instructing the user to get out of the bathtub, in step S807. When receiving this instruction, the relaxation equipment 301 notifies the user of the instruction for instructing the user to get out of the bathtub, i.e., finish taking a bath, through the control unit 503.

In Embodiment 2, the notification may be, for example, a notification using a particular sound or a notification sound. Alternatively, the notification may be displayed in a television in a living room to notify a family member in the living room or other place.

Meanwhile, when the biological information analysis unit 405 does not determine that the heart rate is abnormal (i.e., the obtained heart rate of the user is determined to fall within a normal range) in step S806 (NO in S806), the viewing information management server 300 determines whether or not the program ends in step S808. Specifically, the viewing information management server 300 obtains the position at which program content is being played, and determines whether or not the playback or broadcasting of the program has ended.

When the viewing information management server 300 determines that the playback or broadcasting of the program has ended, in step S808 (YES in step S808), a series of the steps ends.

Meanwhile, when the viewing information management server 300 determines in step S808 that the playback or broadcasting of the program has not yet ended, step S801 is executed again. Thus, the relaxation equipment 301 continues to control so that the user can view the program in a relaxed state until the end of the program.

It should be noted that the present embodiment describes the control of the relaxation equipment 301 using a user model based on stored program information including biological information. However, the control is not limited to this control.

For instance, the viewing information management server 300 stores operation histories when a program is being played back (or broadcasted). The operation histories relate to the operation of the function of the relaxation equipment 301. The relaxation equipment 301 may start, based on the stored operation histories, a function operated by users having similar operation histories when the program is being played back (or broadcasted).

More specifically, when the operation histories are obtained, which represent that many of the users who viewed the same program which the user is viewing started using the function of jetted bathtub while viewing a particular scene of the program, the relaxation equipment 301 performs the control of starting the function of jetted bathtub while the user is viewing the scene. This allows the user to enjoy, at the best timing, the function of jetted bathtub which was operated for relaxing by many users who viewed the same program.

Thus, according to the method of controlling relaxation equipment in the present embodiment, the relaxation equipment is controlled so that the biological value of the user at the end time of the program approximates a biological value included in a user model. When the user model represents a transition in the biological value of a user who can relax during the program, the relaxation equipment is controlled so that the level of relax which the user feels increases during the program and the user finishes viewing the program and using the relaxation equipment in a relaxed state. Thus, the method of controlling can relax the user along with the progress of the program.

Moreover, the relaxation equipment is controlled so that the transition in the biological value of the user during the program approximates the transition in biological value in the user model. Thus, the method of controlling can relax the user along with the progress of the program.

Moreover, the relaxation equipment displays an obtained biological value and a predicted transition in the biological value of the user. By viewing the displayed biological value and its transition, not only the user can check her or his own biological value, but also a person other than the user can check the biological value of the user.

Moreover, the user can relax by getting into a bathtub, which is the relaxation equipment, i.e., by taking a bath in the relaxation equipment.

Moreover, the relaxation equipment controls the temperature of hot water in the bathtub, i.e., the relaxation equipment. In this case, the heart rate of the user is used as the biological value of the user. That is, the relaxation equipment can relax the user taking a bath while viewing a program, based on a transition in heart rate in a user model and the obtained heart rate of the user.

Moreover, specifically, the temperature of hot water in the bathtub, i.e., the relaxation equipment can be controlled based on the heart rate of the user.

Embodiment 3

The present embodiment describes the example in which the viewing information management server 300 controls a home device 901 so that a user can view a program in a relaxed state while using other relaxation equipment, successively after finishing viewing the program content while using the relaxation equipment 301.

Figure 9:
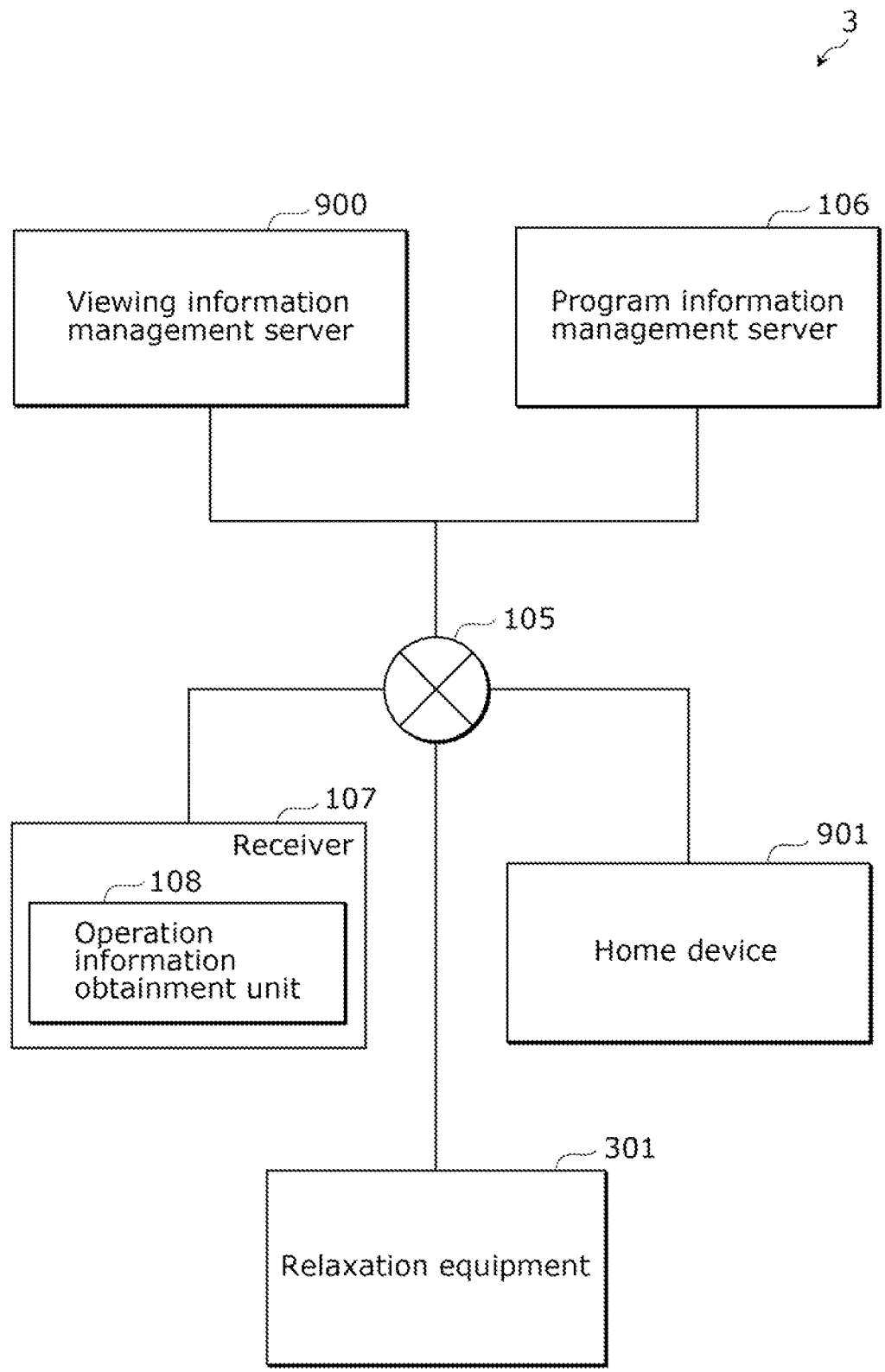
FIG. 9 is a network chart illustrating an example of a control system in Embodiment 3.

FIG. 9 is a network diagram illustrating an example of a control system in the present embodiment.

As illustrated in FIG. 9, a control system 3 includes a viewing information management server 900, relaxation equipment 301, a program information management server 106, a receiver 107, and the home device 901. These devices or servers can mutually communicate via a communication network 105 such as the Internet or an intranet. That is, the relaxation equipment 301 can communicate with the viewing information management server 900 via the communication network 105 such as the Internet or an intra net.

Here, the following describes an example in which the relaxation equipment 301 is a bathtub or a bathroom. It should be noted that the relaxation equipment 301 does not have to be the bathroom or bathtub. The relaxation equipment 301 may be a massage chair or a mist sauna.

The program information management server 106 the relaxation equipment 301, the receiver 107, and the operation information obtainment unit 108 are similar to those illustrated in FIG. 3 in Embodiment 2. Therefore, the explanation for these devices will be omitted here.

The home device 901 can communicate with the viewing information management server 900 via the communication network 105 such as the Internet or an intranet. The operation status of the home device 901 is transmitted to the viewing information management server 900 via the network. The home device 901 is, for example, an air-conditioner in a living room or an electric fan. That is, the operation status of the home device 901 can be monitored and changed by a remote device via a communication network. The operation status of the air-conditioner includes an operation mode such as cooling, heating, or dehumidification or the setting of air quantity. Moreover, the operation status of the electric fan includes the setting of air quantity.

Figure 10:
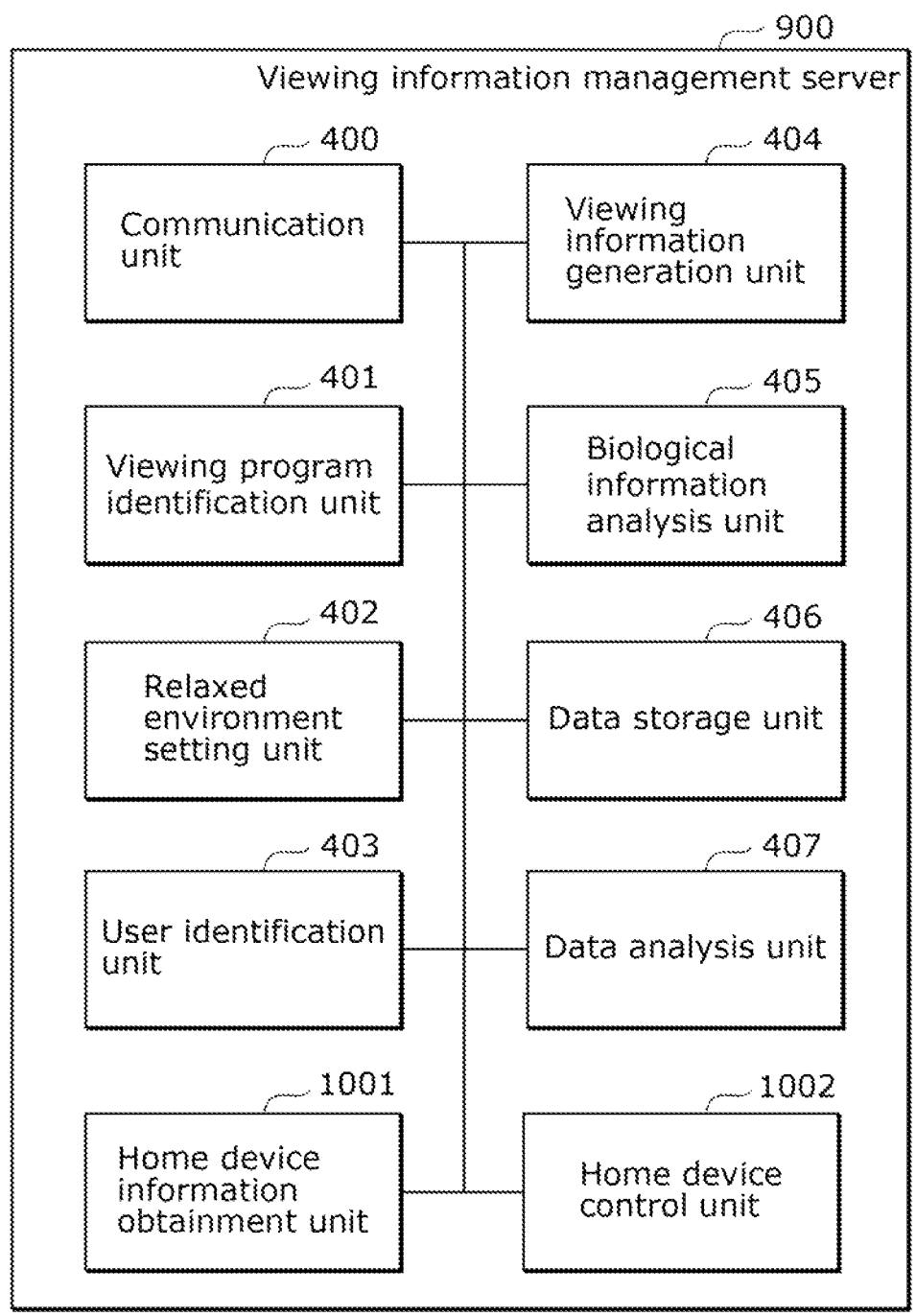
FIG. 10 is a block diagram illustrating an example of a viewing information management server in Embodiment 3.

With reference to FIG. 10, the following describes the configuration of the viewing information management server 900.

FIG. 10 is a block diagram illustrating an example of a viewing information management server in the present embodiment.

The viewing information management server 900 includes a communication unit 400, a viewing program identification unit 401, a relaxed environment setting unit 402, a user identification unit 403, a viewing information generation unit 404, a biological information analysis unit 405, a data storage unit 406, a data analysis unit 407, a home device information obtainment unit 1001, and a home device control unit 1002.

The communication unit 400, the viewing program identification unit 401, the relaxed environment setting unit 402, the user identification unit 403, the viewing information generation unit 404, the biological information analysis unit 405, the data storage unit 406, and the data analysis unit 407 are similar to those described in Embodiment 2. Therefore, the detailed explanation for these units will be omitted in Embodiment 3.

The home device information obtainment unit 1001 obtains the operation status or setting information of the home device 901 which is transmitted from the home device 901.

The home device information obtainment unit 1001 controls the home device 901, based on stored program information including biological information, a user model created by the data analysis unit 407, information on the relaxation equipment 301, and information on the home device obtained from the home device 901. When the home device 901 is an air-conditioner in a living room, the home device information obtainment unit 1001 obtains the operation status or settings of the air-conditioner as home information. Specifically, the information on the relaxation equipment 301 is the temperature of a bathtub or the temperature of a bathroom.

The home device control unit 1002 controls the temperature setting of the air-conditioner or ON/OFF of the operation.

Figure 11:
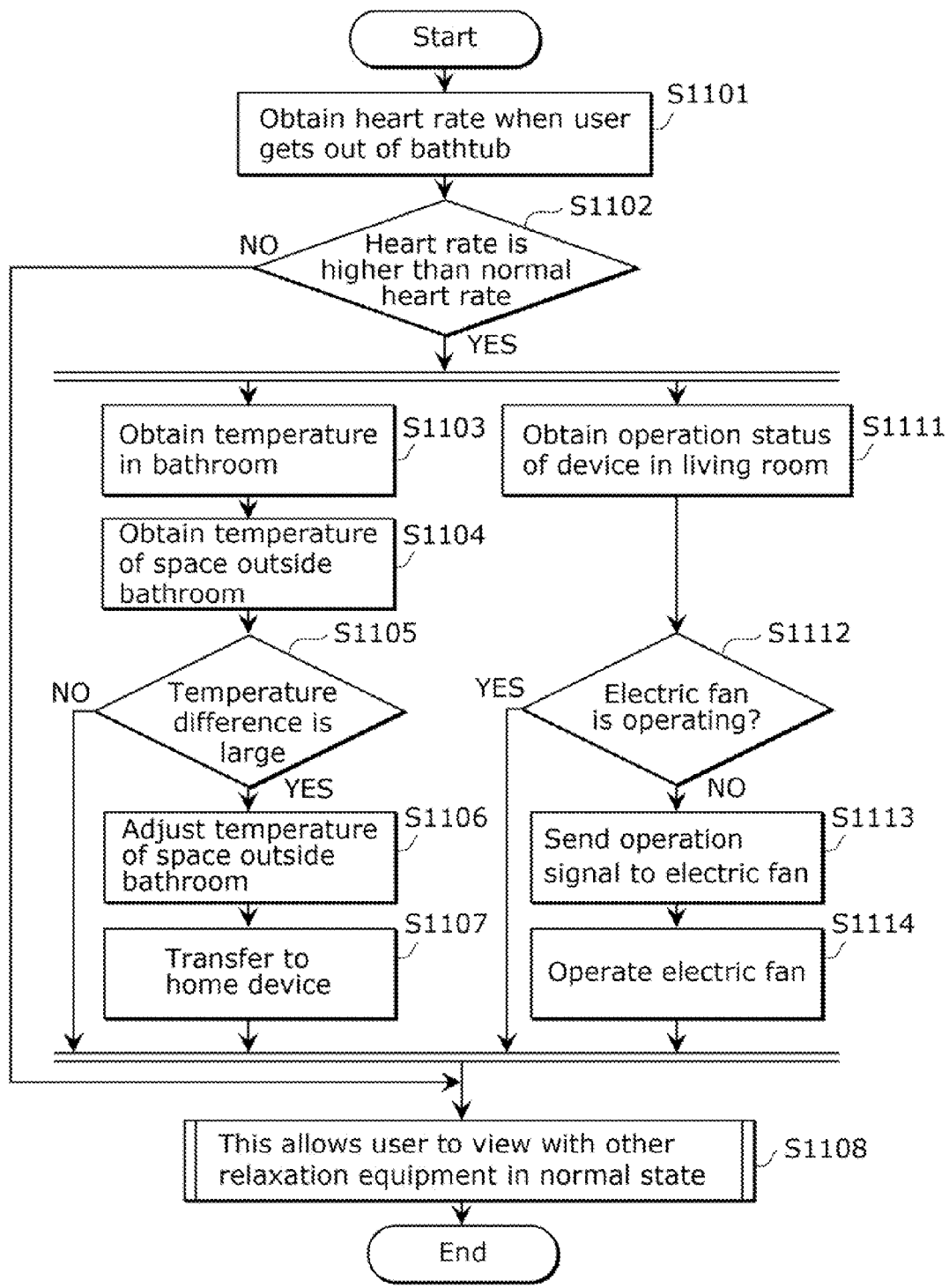
FIG. 11 is a flowchart illustrating an example of the operation of a control system in Embodiment 3.

With reference to FIG. 11, the following describes the operation in which the viewing information management server 900 in the present embodiment controls the home device 901 based on the stored program information including biological information.

FIG. 11 is a flowchart illustrating an example of the operation of the control system in Embodiment 3. FIG. 11 illustrates a procedure when a user, who viewed a program in the bathroom, moves to a space where a home device located outside a bathroom is installed.

It should be noted that the generation processing of program information including biological information when the user is taking a bath and the control processing for relaxation equipment based on stored program information including biological information are similar to those described in Embodiment 2. Therefore, the detailed explanation for these will be omitted in the present embodiment.

When in step S1101, the biological information obtainment unit 502 of the relaxation equipment 301 detects that the user is about to get out of the bathtub, heart rate information at this time is obtained and transmitted to the viewing information management server 900. The viewing information management server 900 obtains the biological information via the communication unit 400. In Embodiment 3, the biological information is, for example, a numeral value representing a heart rate.

In step S1102, the viewing information management server 900 compares the obtained biological information (heart rate) and the stored program information including biological information, to determine whether or not the heart rate when the user gets out of the bathtub is higher than an average value obtained from the stored program information including biological information.

When it is determined in step S1102 that the heart rate, which is the obtained biological information, is higher than the average value obtained from the stored program information including biological information, the control of an air-conditioner in a living room (steps S1103 to S1107) and the control of an electric fan (steps S1111 to S1114) are performed.

The following describes the control of the air-conditioner in the living room.

In step S1103, the relaxation equipment 301 obtains the temperature of the bathroom (S1103).

In step S1104, the home device 901 obtains the temperature of the space outside the bathroom, and transmits the temperature to the viewing information management server 900. Specifically, the temperature of the space outside the bathroom is the temperature of the living room or a path (corridor) from the relaxation equipment 301 to the living room.

In step S1105, the viewing information management server 900 calculates the temperature difference between the temperature obtained by the home device 901 and the temperature of the bathroom obtained by the relaxation equipment 301, and determines whether or not the calculated temperature difference is greater than a predetermined value.

When it is determined in step S1105 that the temperature difference is greater than the predetermined value (YES in step S1105), the temperature of the space outside the bathroom is adjusted. The temperature is adjusted to prevent an increase in the physical burden of the user and an increase in heart rate.

Specifically, in step S1106, the home device control unit 1002 corrects the setting value of the home device 901 which is set as the temperature of the space outside the bathroom, to decrease the temperature difference between the temperature of the bathroom and the temperature of the space outside the bathroom.

In step S1107, the home device control unit 1002 transmits the corrected setting value to the home device 901. When receiving the setting value, the home device 901 operates in accordance with the setting value.

The following describes the control of the electric fan.

In step S1111, the home device information obtainment unit 1001 obtains the operation status of a home device in the living room. Specifically, the home device information obtainment unit 1001 checks the operation status of the electric fan whose air quantity can be adjusted.

In step S1112, the viewing information management server 900 determines whether or not the electric fan is operating. When the viewing information management server 900 determines that the electric fan is not operating (NO in S1112), the viewing information management server 900 transmits control information including an operation signal to the electric fan so as to gradually cool down the body of the user who got out of the bathroom, in step S1113.

In step S1114, when receiving the control information including an operation signal, the home device 901 (electric fan) starts operating.

The following processing procedure enables user's body to shift to a normal state even if the user who was out from a bathroom does not perform an explicit operation on a home device. After that, it is possible to encourage the user, who was out from the bathroom, to use other relaxation equipment. This allows the user to continue to view a program. The other relaxation equipment is, for example, a massage chair.

Thus, according to the method of controlling relaxation equipment in the present embodiment, the relaxation equipment gradually changes the biological value of the user who finished using the relaxation equipment by controlling electrical equipment in a home where the relaxation equipment is installed. This can reduce the physical burden of the user who finished using the relaxation equipment.

The following describes a display image displayed by a control system in each embodiment. It should be noted that a display image, which will be described later, is used for showing a user the status of control performed by the control system. However, the display image is not an essential element.

Figure 12:
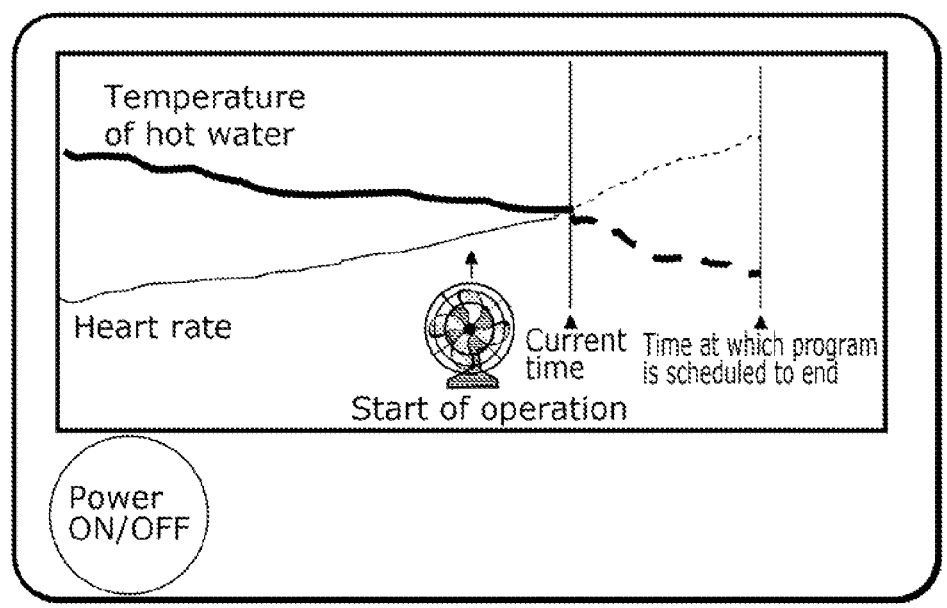
FIG. 12 illustrates a first example of a display image in a control system.
Figure 12:
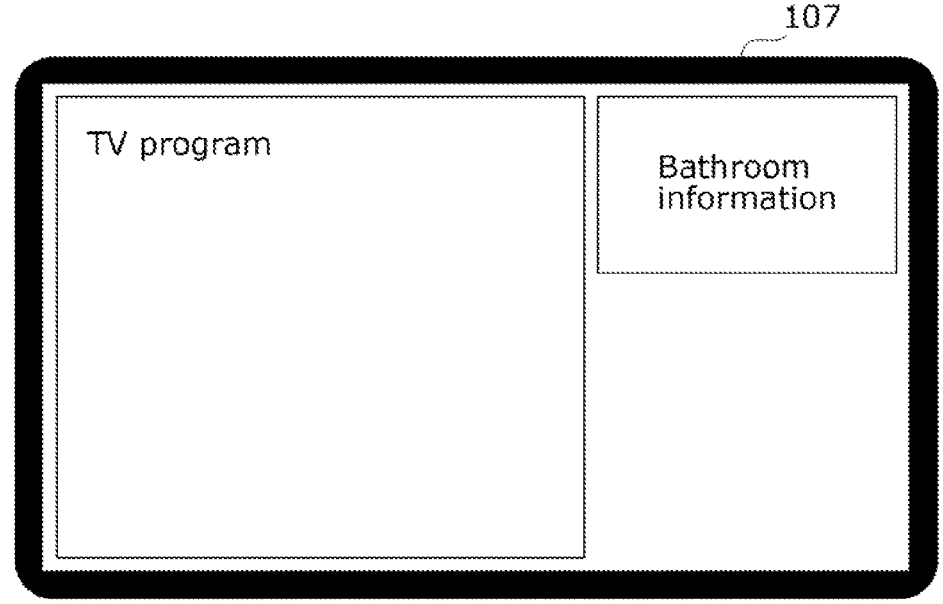

FIG. 12 illustrates a first example of the display image in the control system.

(a) in FIG. 12 is the display image displayed when the control system is controlling the temperature of hot water in a bathroom. Specifically, (a) in FIG. 12 is the display image displayed when the control system is performing the temperature adjustment control in step S805 in FIG. 8A. It should be noted that this display image is achieved as the operation panel of the control system. However, the display image may be achieved as the operation panel of a water heater.

In (a) in FIG. 12, the horizontal axis represents elapsed time while the vertical axis represents heart rate and the temperature of hot water. In (a) in FIG. 12, solid lines represent a transition in the heart rate of the user and a transition in the temperature of hot water until current time. Moreover, the broken lines represent the heart rate and the prediction value of the temperature of hot water from the current time until the end of the program. It is understood from these broken lines that the heart rate is expected to transition as displayed if the temperature of hot water transitions as displayed. It is also said that information obtained from a user model is displayed in a way easy to understand for a user. Moreover, the start of the operation of the ventilation fan in a bathroom and its time are shown by an icon and words.

(b) in FIG. 12 is a figure for explaining an image displayed in the receiver 107. A TV program is normally displayed in the entire screen of a receiver. However, when information is provided from a bathroom, which is relaxation equipment, the display area of the TV program is reduced, and the information provided from the bathroom ("bathroom information") is displayed in a display area generated by reducing the display area of the TV program. The information provided from the bathroom is, for example, identical to the image illustrated in (a) in FIG. 12. Thus, the user can visually check the information provided from the bathroom while viewing the TV program. It should be noted that the display image may be displayed in a display device other than the receiver 107, such as a television in a living room (not illustrated in the figure). Displaying the display image in the living room allows a person in the living room to know the condition of the user in the bathroom.

Figure 13:
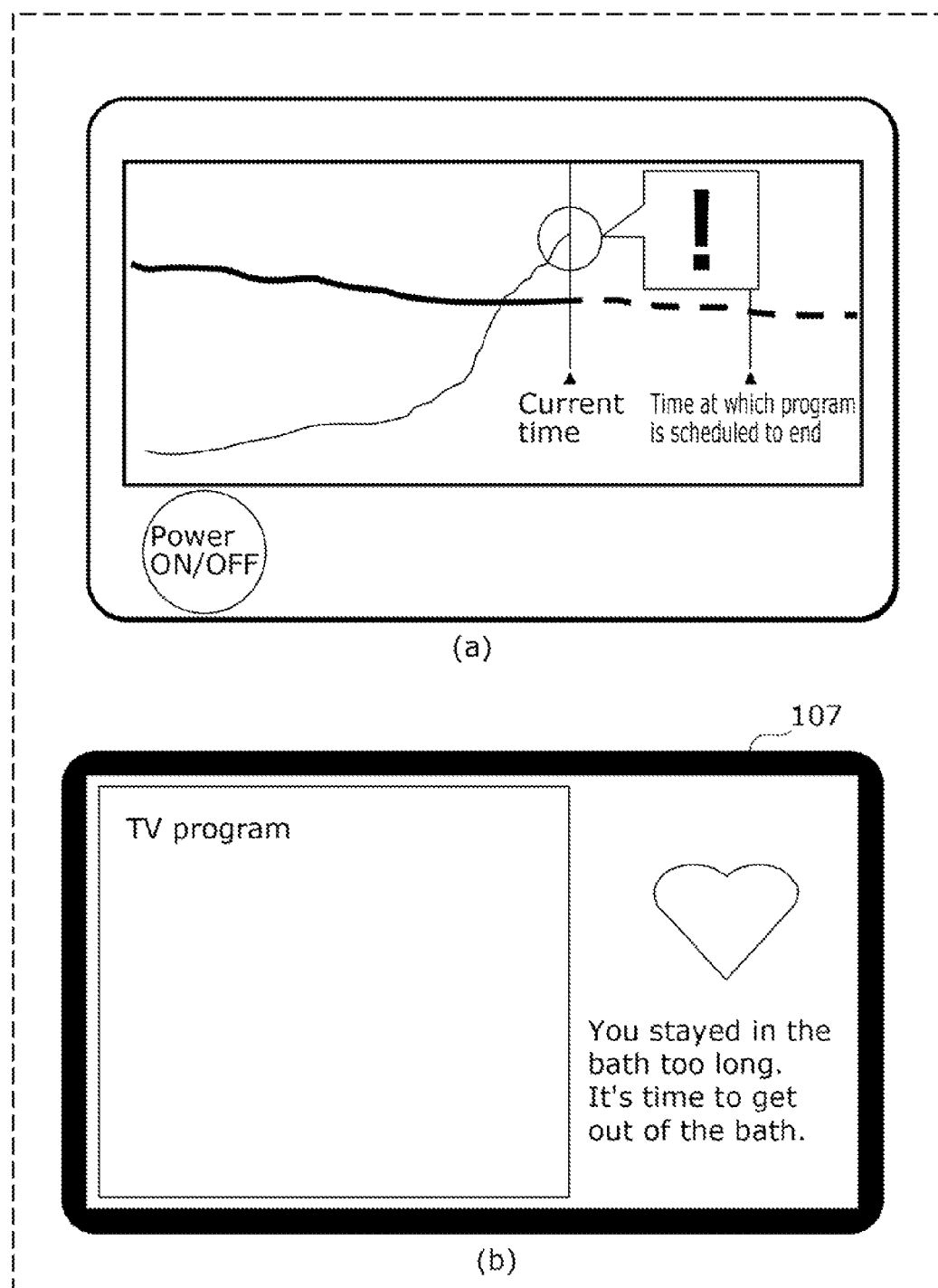
FIG. 13 illustrates a second example of a display image in a control system.

FIG. 13 illustrates a second example of the display image in the control system.

(a) in FIG. 13 is the display image displayed when the control system is controlling the temperature of hot water in the bathroom. Specifically, (a) in FIG. 13 is the display image when the control system detects abnormal heart rate in step S806 in FIG. 8A. It should be noted that this display image is achieved as the operation panel of the control system. However, the display image may be achieved as the operation panel of a water heater.

As with (a) in FIG. 12, (a) in FIG. 13 illustrates a transition in the heart rate of the user and a transition in the temperature of hot water. Moreover, it is clear from the figure that at the current time, the heart rate of the user largely deviates from the biological value obtained from a user model. The control system may display, for example, an exclamation mark (!) to emphasize the significant deviation.

(b) in FIG. 13 is a figure for explaining an image displayed in the receiver 107. As with (b) in FIG. 12, (b) in FIG. 13 includes the reduced display area of a TV program. A message for instructing the user to get out of a bathtub (or bathroom) ("You stayed in the bath too long. Its time to get out of the bath.") is displayed in the area next to the display area of the TV program. It should be noted that as with (b) in FIG. 13, the display image may be displayed in a television (not illustrated in the figure) in a living room.

Figure 14:
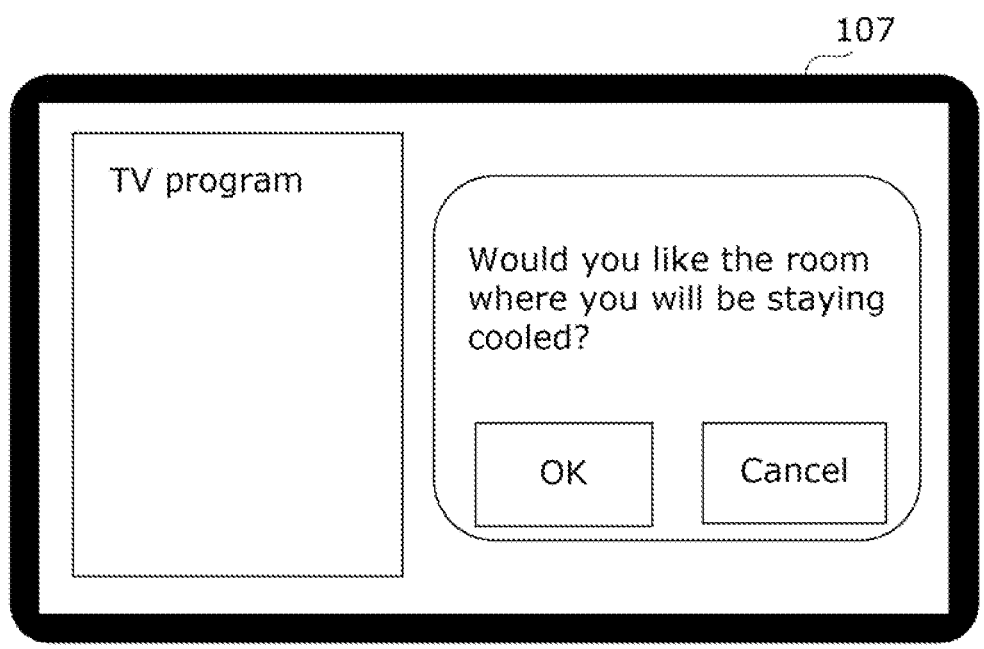
FIG. 14 illustrates a third example of a display image in a control system.

FIG. 14 illustrates a third example of the display image in the control system.

FIG. 14 is a figure for explaining an image displayed in the receiver 107. Specifically, FIG. 14 illustrates the display image when the control system detects that the heart rate of the user is higher than a normal heart rate in step S1102 in FIG. 11. As with (b) in FIG. 12, FIG. 14 includes the reduced display area of a TV program. The control system provides a message for asking the user whether or not to operate a home device provided outside the bathtub (or bathroom) ("Would you like the room where you will be staying cooled?") in the area next to the display area of the TV program.

Figure 15:
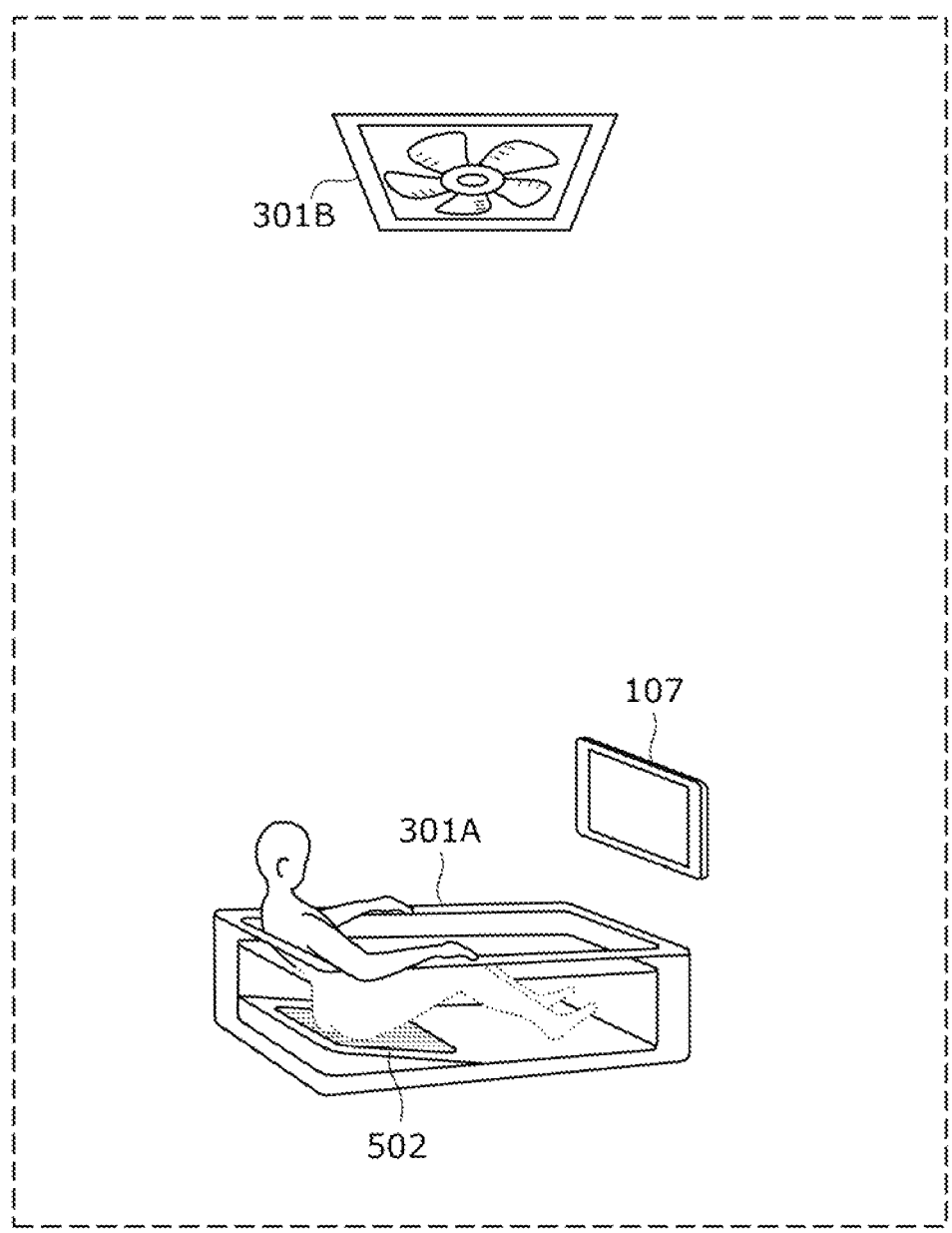
FIG. 15 is an example of the overview diagram of a control system.

FIG. 15 is an example of the overview diagram of the control system. As illustrated in FIG. 15, the control system includes relaxation equipment 301A (bathtub), relaxation equipment 3018 (ventilation fan), a receiver 107, and a biological information obtainment unit 502. The user views the images of a program being played by the receiver 107 while taking a bath in the relaxation equipment 301A (bathtub). The biological information obtainment unit 502 obtains biological information including the heart rate of the user. The control system controls the relaxation equipment 301A and 3016 such that the user can view the program in a relaxed state until the end of the program being played by the receiver 107.

It should be noted that Embodiments 1, 2, and 3 described a bathroom and a bathtub as examples of the relaxation equipment. However, the relaxation equipment is not limited to these. The relaxation equipment may be a massage chair. The user may view program content while using the massage chair, and then use a bathtub.

Moreover, the relaxation equipment may be a sauna of sufficient size to accommodate more than one person. That is when more than one user is viewing a program in the sauna, pieces of biological information on the users viewing the program may be obtained, and the obtained pieces of biological information may be added to the program.

Moreover, the above describes that a sensor is used for obtaining biological information with the relaxation equipment. However, this is not limited to the sensor. For example, an imaging sensor capable of measuring the temperature of a user, using thermography may be used.

It should be noted that Embodiments 1, 2, and 3 describe that the viewing information management server controls the settings of the relaxation equipment such as the temperatures of a bathroom and a bathtub. However, other control is also possible.

For example, the humidity of the bathroom may be controlled. Moreover, control information for lowering the humidity of the bathroom may suggest operating a ventilation fan in the bathroom.

It should be noted that in Embodiments 1, 2, and 3, the viewing information management server controls home devices such as an air-conditioner in a living room and an electric fan. However, other control is also possible.

For instance, when determining that the heart rate of the user, who viewed a program in the bathtub and is about to get out of the bathtub, is close to the heart rate obtained when the user falls asleep, the viewing information management server may perform a control such that the user who got out of a bathroom is likely to fall asleep, rather than waking up the user. In this case, the viewing information management server may provide the environment in which the user can fall asleep in a relaxed state, by sending control information for instructing lighting equipment in a home to reduce light.

It should be noted that Embodiments 1, 2, and 3 describe the processing which allows the user to view a program until the end of the program, using relaxation equipment. However, other processing is also possible.

For example, when the user got out of the bathtub before the program ends and when the played program is a recorded program, control may be performed such that the user can continue to view the program later. That is, when the user got out of the bathtub before the program ends, the scene of the program at the timing when the user got out of the bathtub is recorded. Moreover, when the played program is broadcast content, the viewing information management server instructs the program information management server to record the program being played. When receiving the instruction from the viewing information management server, the program information server instructs a receiver to record the program being played. Control is performed such that the user who got out of the bathtub can continue to view the program which the user viewed halfway, with the receiver represented by a television in a living room.

It should be noted that Embodiments 1, 2, and 3 describe a television as an example of the receiver. However, the receiver is not limited to the television. For example, program content may be viewed with a smart phone or a tablet terminator. Moreover, content to be viewed by a user may be a web page, an electronic book, or music content.

It should be noted that in Embodiments 1, 2, and 3 describe only one viewing information management server. However, more than one server may operate through distributed coordination. Here, more than one server may manage program information including biological information to be stored, through distributed management.

It should be noted that in Embodiments 1, 2, and 3, program content to be viewed by a user while using relaxation equipment is selected by the user operating a receiver. However, other selection is also possible. For instance, the playback of the program content which was viewed by many users while using relaxation equipment may be recommended to the user, and the user may be encouraged to playback the program content. Moreover, a program viewed by a user whose biological information is close to the biological information of the user obtained by the relaxation equipment may be recommended.

It should be noted that program content may be recorded by a user, or a program the recording of which was reserved by many of the users who views programs while using relaxation equipment on a daily basis may be automatically recorded.

It should be noted that in the above embodiments, each structural element may be a dedicated hardware or may be achieved by executing a software program suitable for each structural element. Each structural element may be achieved by a program execution unit such as a CPU or a processor reading and executing a software program recorded on a recording medium such as a hard disk or a semiconductor memory. Here, the software program which achieves the control system in the relaxation equipment in the above embodiments and others is a program as described below.

That is, this program causes a computer to execute a method of controlling relaxation equipment capable of changing a biological value of a user, the method including: obtaining a user model including a transition in biological value within a period from a start time to an end time of a program; obtaining a first biological value of the user viewing the program; and controlling the relaxation equipment such that the biological value of the user at the end time approximates a second biological value included in the user model, which is a value at the end time, based on the first biological value and the second biological value.

A control system for relaxation equipment according to one or more than one aspect was described above based on the embodiments. However, the present invention is not limited to the embodiments. One or more than one aspect may include an embodiment obtained by making various changes, which those skilled in the art would conceive, to the present embodiment or an embodiment obtained by combining structural elements in different embodiments, unless such embodiment does not depart from the scope of the present invention,

INDUSTRIAL APPLICABILITY

The control system of relaxation equipment, the method of controlling the relaxation equipment, and the method of creating a user model according to the present invention can easily measure everyday the biological information of a user viewing a program in a unified environment where the user can relax.

That is, the present invention is applicable to, for example, a device which a user uses while viewing content in a relaxed state, such as a bathtub apparatus or a massage chair. Moreover, such device can be used managerially, continuously, and repeatedly in the industry which manufactures, sells, provides, and uses the bathtub apparatus and others.

REFERENCE SIGNS LIST 1, 2, 3 control system
100, 300, 900 viewing information management server
101 viewing information generation unit
102 data storage unit
103, 301, 301A, 301B relaxation equipment
104 biological information obtainment unit
105 communication network
106 program information management server
107 receiver
108 operation information obtainment unit
109 data analysis unit
400, 501 communication unit
401 viewing program identification unit
402 relaxed environment setting unit
403 user identification unit
404 viewing information generation unit
405 biological information analysis unit
406 data storage unit
407 data analysis unit
502 biological information obtainment unit
503 control unit
901 home device
1001 home device information obtainment unit
1002 home device control unit

The invention claimed is:

1. A method of controlling relaxation equipment capable of changing a biological value of a user, the method comprising:
obtaining a first biological value of the user viewing a program;
transmitting the first biological value to a management server;
determining, at the management server, the user from the obtained first biological value, the user being determined by comparing a pre-obtained weight information and first biological value;
determining, at the management server, a user model to which the determined user belongs, the user model being determined based on history of programs viewed by the user; and controlling the relaxation equipment, based on the first biological value of the user and a transition in a second biological value included in the user model, to cause the second biological value of the user to undergo a transition during a period from a time of obtaining the first biological value to the end time of the program so that the second biological value of the user falls within a permissible range of the transition in the second biological value included in the user model.

2. The method of controlling relaxation equipment according to claim 1,
wherein the controlling includes controlling the relaxation equipment, based on the first biological value of the user and the transition in the second biological value included in the user model at a predetermined time during the program, to change the second biological value of the user at the predetermined time during the program to approximate the transition in the second biological value included in the user model at the predetermined time during the program.

3. The method of controlling relaxation equipment according to claim 2, further comprising:
displaying the first biological value and a transition in the second biological value of the user which is predicted from the first biological value and the second transition in the biological value included in the user model.

4. The method of controlling relaxation equipment according to claim 1, further comprising:
controlling electrical equipment in a home where the relaxation equipment is placed to gradually change the second biological value of the user after the program ends.

5. The method of controlling relaxation equipment according to claim 1,
wherein the relaxation equipment includes a bathtub which the user is able to get into.

6. The method of controlling relaxation equipment according to claim 5, wherein the second biological value is a heart rate, and
in the controlling, the relaxation equipment is controlled by controlling a temperature of hot water in the bathtub.

7. The method of controlling relaxation equipment according to claim 6, wherein in the controlling, when the heart rate of the user at the end time of the program is lower than the transition in the second biological value included in the user model at the end time of the program, based on an assumption that the heart rate of the user after the first biological value is obtained transitions from the first biological value in a same way as a heart rate in the user model transitions, the relaxation equipment is controlled by increasing the temperature of hot water in the bathtub.

8. A control system of changing a biological value of a user, the control system comprising:
a management server; and
relaxation equipment that obtains a first biological value of a user viewing the program, and transmits the first biological value to the management server,
wherein the management server (i) determines the user from the obtained first biological value, the user being determined by comparing pre-obtained weight information and the first biological value and (ii) determines a user model to which the determined user belongs, the user model being determined based on a history of programs viewed by the user, and
wherein the relaxation equipment performs control, based on the first biological value of the user and a transition in a second biological value included in the user model, to cause the second biological value of the user to undergo a transition during a period from a time of obtaining the first biological value to the end time of the program so that the second biological value of the user falls within a permissible range of the transition in the second biological value included in the user model.

* * * * *